(12) United States Patent
Malvy et al.

(10) Patent No.: US 7,022,832 B2
(45) Date of Patent: Apr. 4, 2006

(54) OLIGONUCLEOTIDES CONTAINING AN ANTISENSE SEQUENCE STABILIZED BY A SECONDARY STRUCTURE, PHARMACEUTICAL COMPOSITIONS CONTAINING THEM AND METHOD OF BLOCKING GENE EXPRESSION USING THEM

(75) Inventors: Calude Malvy, Boussy-Saint-Antoine (FR); Valerie Helin, Paris (FR); Andrei Maksimenko, Paris (FR); Marina Gottikh, Moscou (RU)

(73) Assignees: Bioalliance Pharma (S.A.), (FR); Centre National de la Recherche Scientifique - CNRS, (FR)

( * ) Notice: Subject to any disclaimer, the term of this patent is extended or adjusted under 35 U.S.C. 154(b) by 456 days.

(21) Appl. No.: 09/949,134

(22) Filed: Sep. 7, 2001

(65) Prior Publication Data

US 2002/0156261 A1    Oct. 24, 2002

Related U.S. Application Data

(63) Continuation of application No. PCT/FR00/00586, filed on Mar. 9, 2000.

(30) Foreign Application Priority Data

Mar. 9, 1999  (FR) .................................. 99 02921

(51) Int. Cl.
    *C07H 21/04* (2006.01)
(52) U.S. Cl. .................................... 536/24.5
(58) Field of Classification Search ................. 514/44; 536/24.5
    See application file for complete search history.

(56) References Cited

FOREIGN PATENT DOCUMENTS

| WO | WO/94/01550 | 1/1994 |
|----|-------------|--------|
| WO | WO 94/12633 | 6/1994 |
| WO | WO 94/23026 | 10/1994 |
| WO | WO 95/29241 | 11/1995 |

OTHER PUBLICATIONS

Wang et al. Antisense and Nucleic Acid Drug Delivery, 2003, vol. 13, p. 169-189.*
Flanagan et al., Nature Biotechnology. vol. 17 p. 48-52 Jan. 1999.*
Opalinska et al. Nature Review, 2002, vol. 1, p. 503-514.*
Agrawal et al. Molecular Medicine Today,2000, vol. 6, p 72-81.*
Green et al. J. Am Coll. Surg., 2000, vol. 191, p 93-105.*
Jen et al. Stem Cells 2000, vol. 18, p 307-319.*
Crooke, Antisense Research and Application, Chapter 1, Springer-Verlag, New York, 1998.*
Branch, TIBS, 1998, vol. 23, p 45-50.*
Sokol, D. L. et al, "Real time detection of DNA-RNA hybridization in living cells", Proc. Natl. Acad. Sci. USA, Sep. 9, 1998, pp. 11538-11543.
Abe, T. et al., "Specific inhibition of influenza virus RNA polymerase and nucleoprotein gene expression by circular dumbdell RNA/DNA chimeric oligonucleotides containing antisense phosphodiester oligonucleotides," Febs Lett 425 (1), Mar. 20, 1998, pp. 91-96.
Barker RH Jr. et al, Plasmodium falciparum: Effect of Chemical Structure on Efficacy and Specificity of Antisense Oligonucleotides against Malaria in Vitro, Experimental Parasitology 88, Jan. 1998, pp. 51-59.
Jolles, B. et al, Opening of the extraordinaril,y stable mini-hairpin d(GCGAAGC), Nucleic Acids Research, vol. 25. No. 22, Nov. 15, 1997, pp. 4608-4613.
Tanaka, Kazuhiro et al., EWS-Flil Antisense Oligodeoxynucleotide Inhibits Proliferation of Human Ewings's Sarcoma and Primitive Neurectodermal Tumor Cells, Journal of Clinical Investigation, vol. 99, No. 2, 1997, pp. 239-247.
Gottikh, M.B. et al, "α-β Chimeric Oligonucleotides Form a New Stable "Snail-like"Structure,", J. Am. Chem. Soc., 1996, 118, pp. 2126-2130.
Tang, J. et al, Self-stabilized antisense oligodexynucleotide phosphorothioates: properties and anti-HIV activity, Nucl. Acids Research, vol. 21, No. 11, 1993, pp. 2729-2735.

* cited by examiner (Continued)

Primary Examiner—Andrew Wang
Assistant Examiner—Tracy Vivlemore
(74) Attorney, Agent, or Firm—DLA Piper Rudnick Gray Cary US LLP

(57) ABSTRACT

Oligonucleotides capable of modifying or inhibiting in vivo or in vitro expression of a target gene wherein the oligonucleotide has an antisense sequence, at least one secondary structure, and optionally a supplementary nucleotide sequence located at one and/or both ends of the antisense sequence and wherein the secondary structure disintegrates upon attachment of the oligonucleotide to a target nucleic acid; a pharmaceutical composition containing such an oligonucleotide as an active ingredient; and a method of treatment using such an oligonucleotide.

6 Claims, 14 Drawing Sheets

Fig. 7

Target Sequences

D (SEQ. ID. NO. 5) 5'-d (CCAGC<u>AGAATCGACACATGGCGTGTTCA</u>ACGCT)-3'

R (SEQ. ID. NO. 6) 5'-r (CCAGC<u>AGAAUCGACACAUGGCGUGUUCA</u>ACGCU)-3'

Antisense Oligonucleotides 21L (SEQ. ID. NO. 7)   5'-TGAACACGCCATGTCGATTCT-3'

55L (SEQ. ID. NO. 8)   5'-T$_2$ACT$_3$CT$_5$GCGTTGAACACGCCATGTCGATTCTT$_5$CT$_5$C$_6$-3'

21PS (SEQ. ID. NO. 9)   5'-T*G*AACACGCCATGTCGATTC*T-3'

H6 (SEQ. ID. NO. 10)
```
5'-TGAACACGCCATGTCGATTCT T
              3'-CTAAGA T
```

H8 (SEQ. ID. NO. 11)
```
5'-TGAACACGCCATGTCGATTCT T
            3'-AGCTAAGA T
```

H10 (SEQ. ID. NO. 12)
```
5'-TGAACACGCCATGTCGATTCT T
          3'-ACAGCTAAGA T
```

Dh6 (SEQ. ID. NO. 13)
```
C TGAACACGCCATGTCGATTCT T
T ACTTGT-5'        3'-CTAAGA T
```

L8 (SEQ. ID. NO. 14)
```
                      ACGC
5'-GCGTA T GAA C         C
3'-CGCAT T CTT A         A
                 GCT G T
```

L10 (SEQ. ID. NO. 15)
```
                        ACGC
5'-GCGCTTA T GAA C          C
3'-CGCGAAT T CTT A          A
                   GCT G T
```

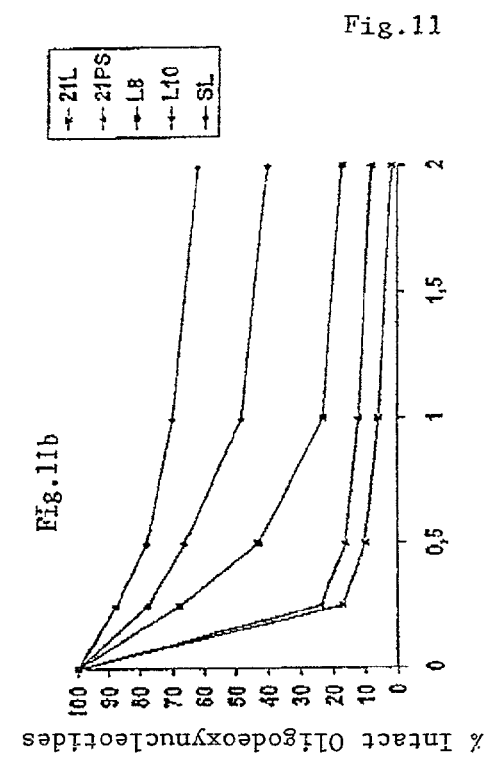
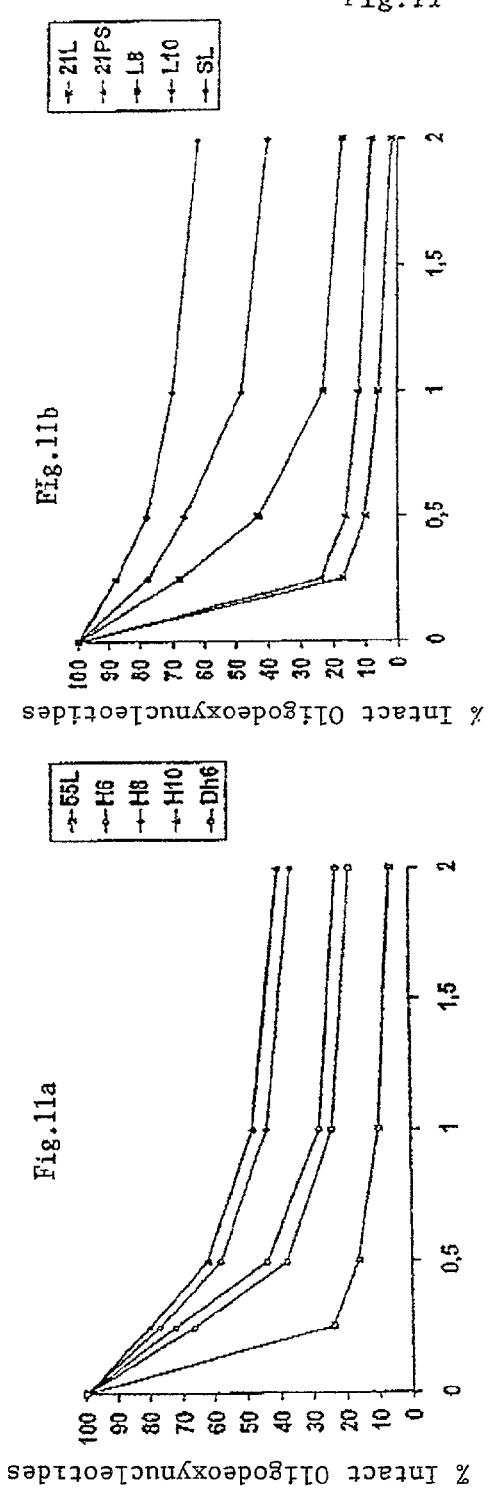
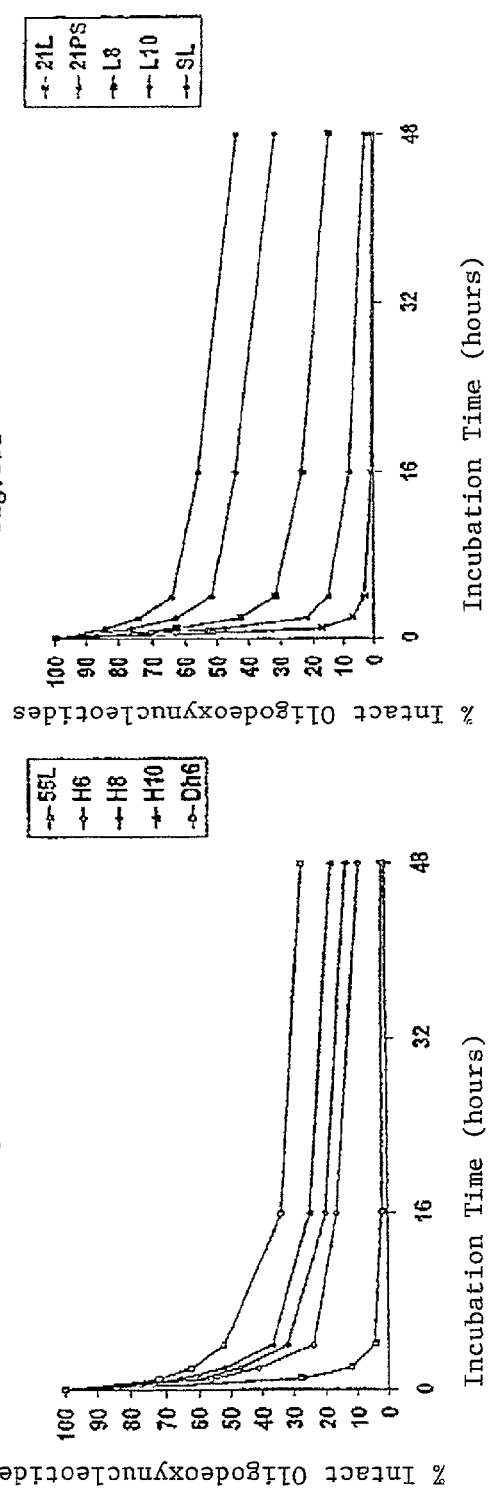
Fig. 11

Fig. 12
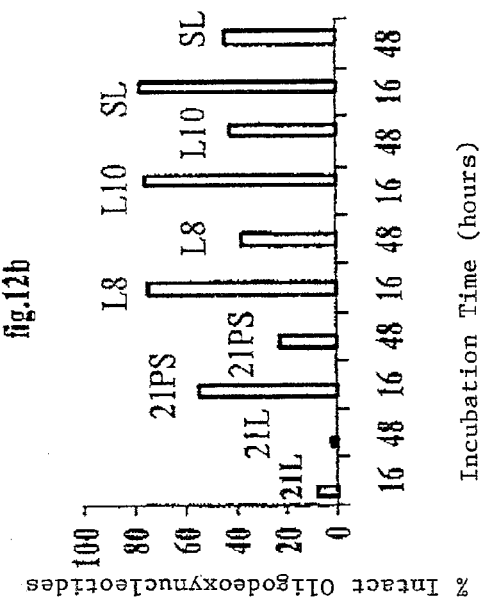
fig.12a
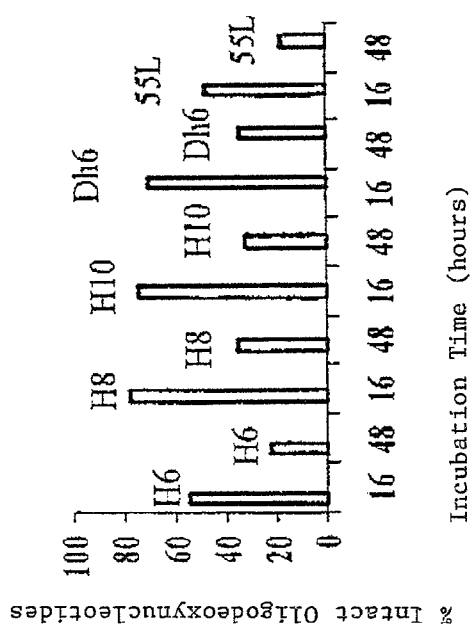
fig.12c
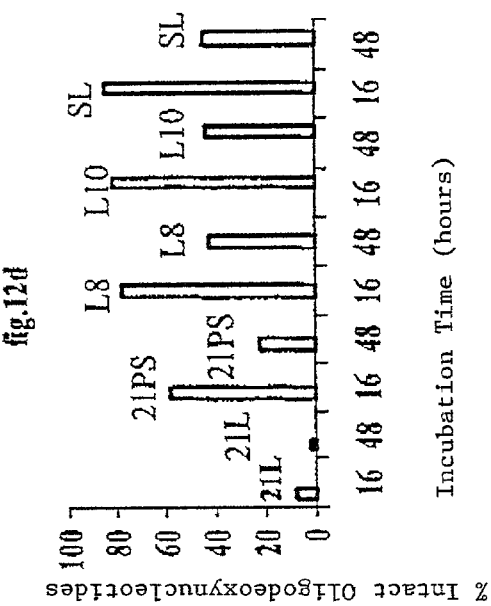
fig.12b
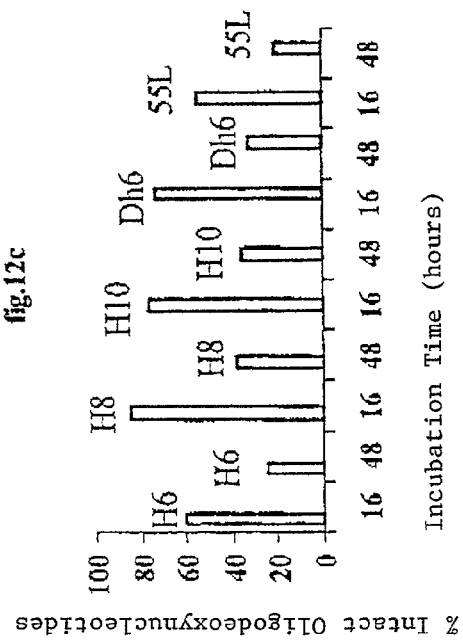
fig.12d

Fig 13

A Phosphodiester Oligonucleotides

Dh INGFp (SEQ. ID. NO. 16)

```
         T CTCGAC-5'    3'-CGGCAG T
    12   T                        T          15-25
         GAGCTGCACGCTGCCGTC
```

Sh-6 INGFp (SEQ. ID. NO. 17)

```
                  3'-CGGCAG T
                            T               15-25
    13   5'-GAGCTGCACGCTGCCGTC
```

L4 INGFp (SEQ. ID. NO. 18)                L2 INGFp (SEQ. ID. NO. 19)

```
    14  5'-GCGA  GCT GCA  C                      5'-GA  GCT GCA  C
        3'-CGCT  GC  CGT C G   15-25        15   3'-CT      CGT  G    5-10
                                                       GC      C
```

L7 INGFp (SEQ. ID. NO. 20)

```
    16  5'-GCGTAGA  GCT GCA  C
        3'-CGCATCT  GC  CGT  G                   10-15
                           C
```

C7 INGFp (negative control) (SEQ. ID. NO. 21)

```
                      GCC  GTC
    17  5'-GCGTAGA            A
        3'-CGCATCT            C                    0
                      GC  TGC  G
```

B Phosphorothioate Oligonucleotides

L2 INGFp 2S (SEQ. ID. NO. 22)          L4 INGFp 2S (SEQ. ID. NO. 23)

```
    18  5'-G*A*  GCT GCA  C                   5'-G*C*GA  GCT GCA  C
        3'-C*T*  GC  CGT  G   65-80      19   3'-C*G*CT  GCG CGT  G    30-40
                           C                                      C
```

SDh INGFp (SEQ. ID. NO. 24)

```
              A    3'-G*G*CAG C
    20   C          CGCTG C C GTC  T        15-30
         G    T  CGA* G*-5'         C
```

21 PS (negative control) (SEQ. ID. NO. 9)

5'-T*G*AACACGCCATGTCGATTC*T*-3'                    0

---
*: phosphorothioate group

Fig.15
Fig.15A
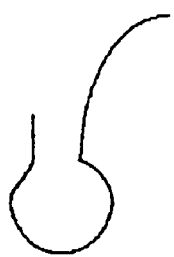
A
Fig.15B
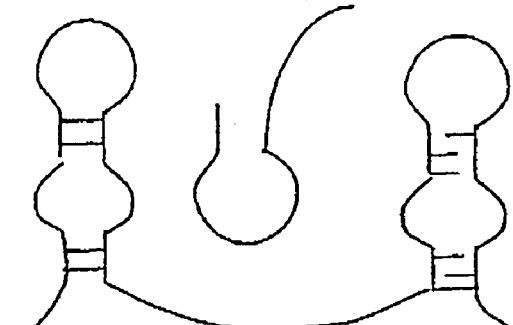
B
Fig.16
Fig.16A
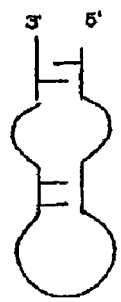
A
Fig.16B
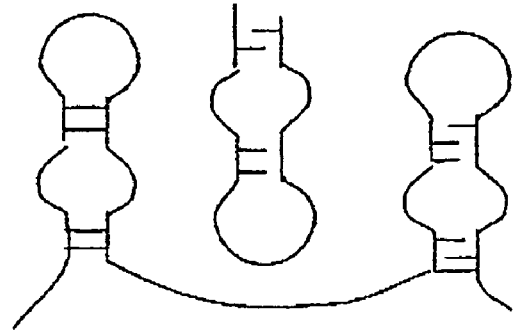
B
Fig.17
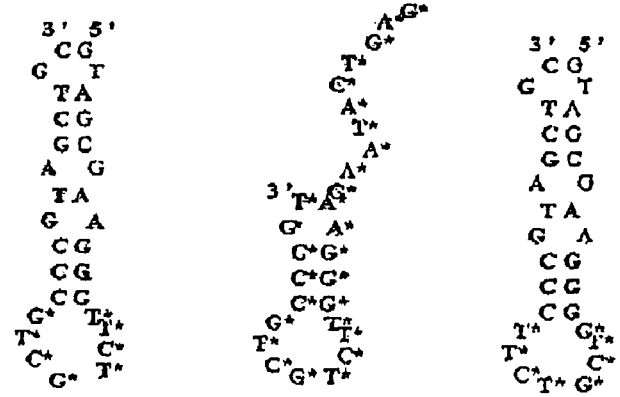
antisense EF 3008AS    antisense EF 2929AS    control EF 3008RLS (SEQ. ID. NO. 3)
control EF 2929CS (SEQ. ID.NO. 4)
5'_C*T*C*A*G*C*T*T*A*C*T*A*C*T*C*A*G*A*T*
G*A*T*C*G*G*C*T*C*A*_3'

Fig.18
fig.18a
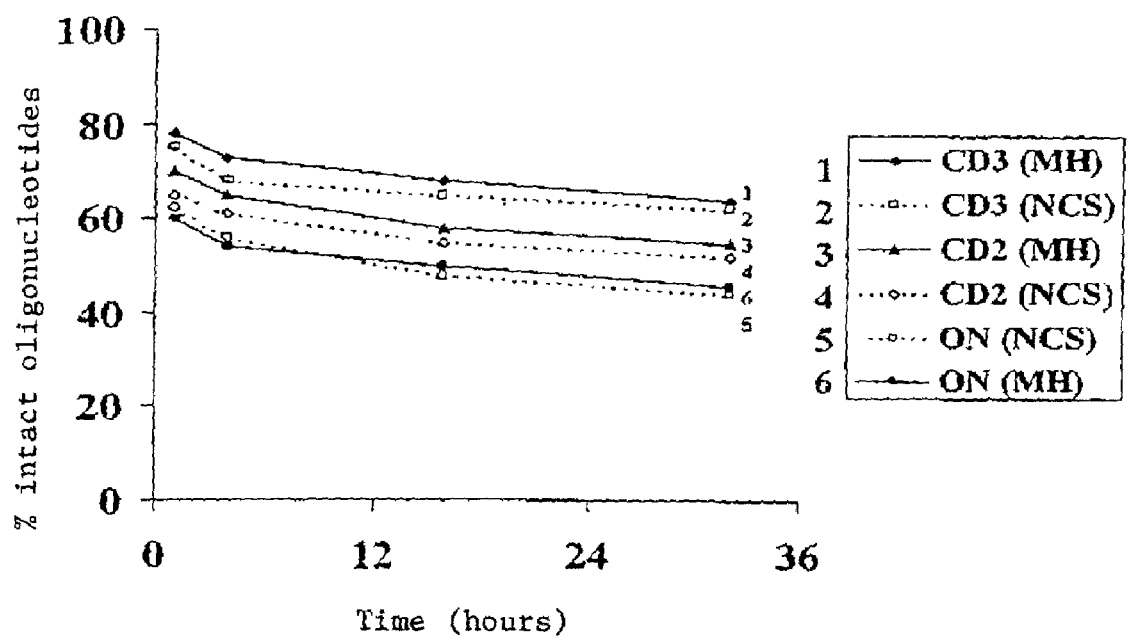
fig.18b
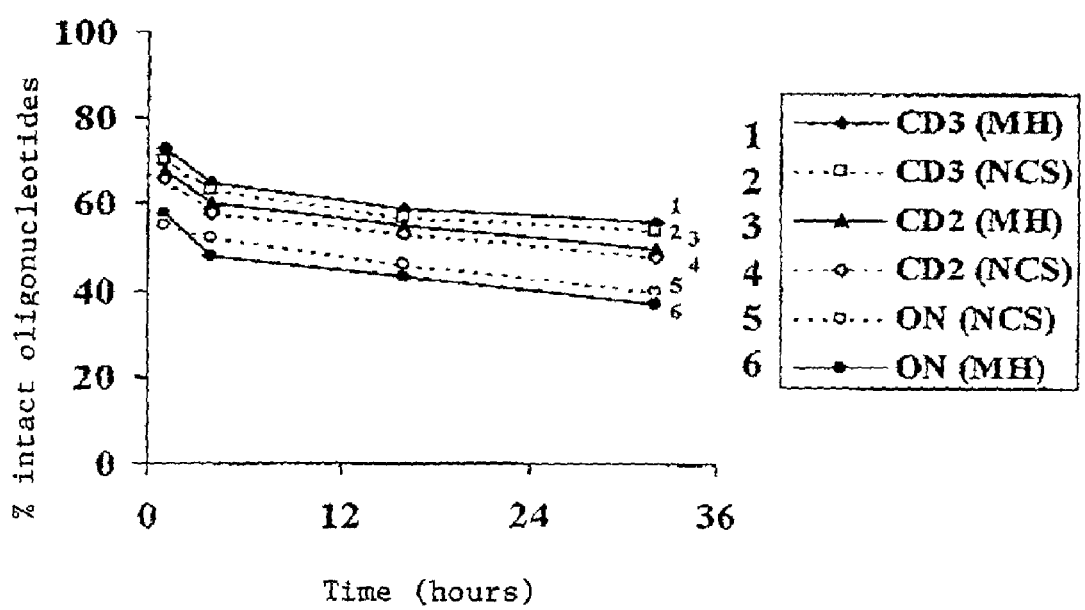

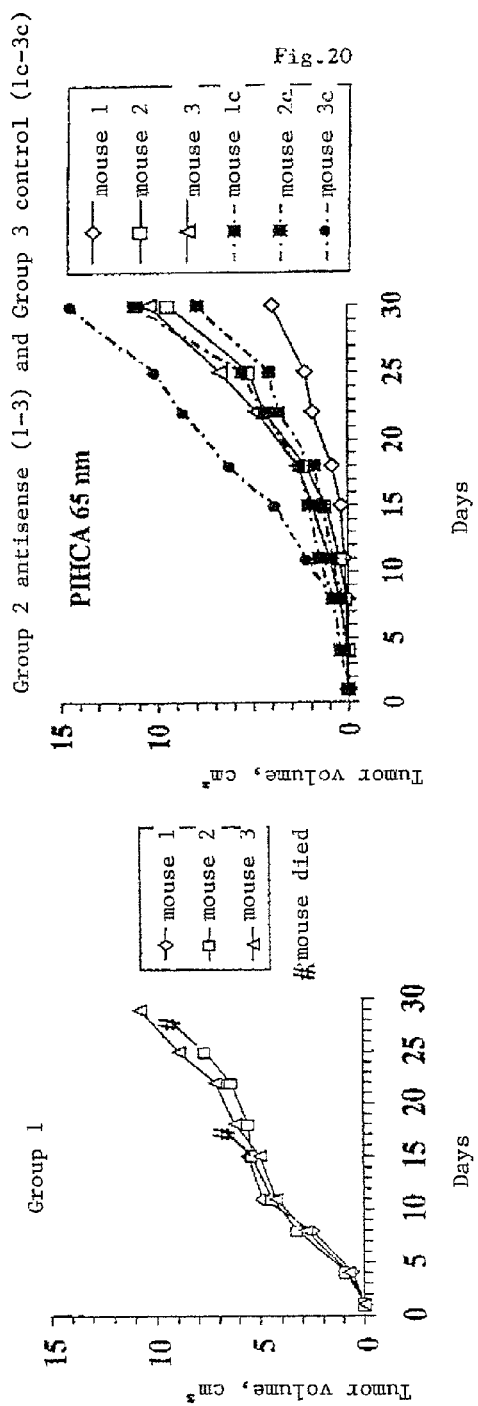
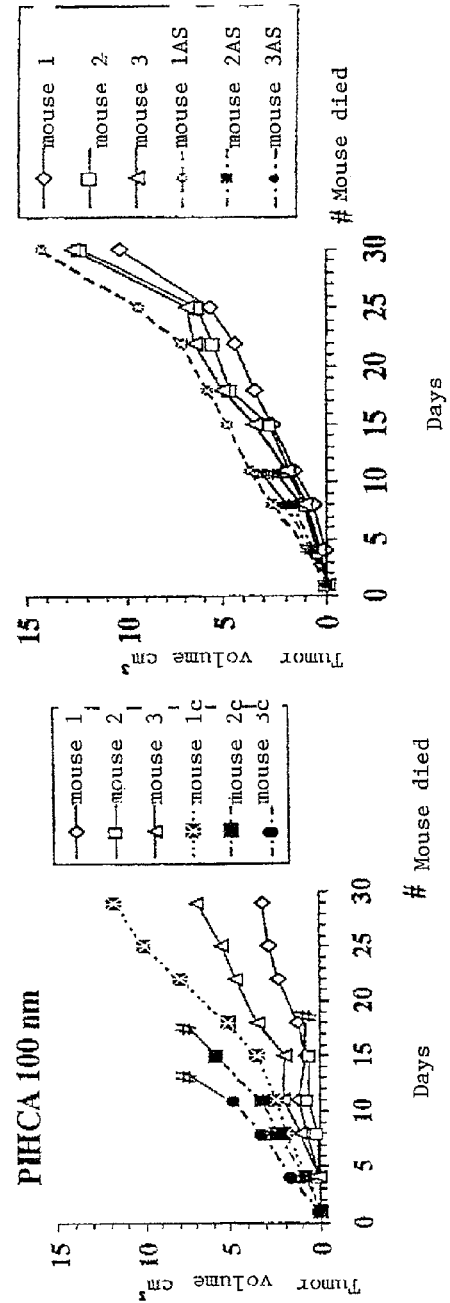
Fig. 20

Fig.21
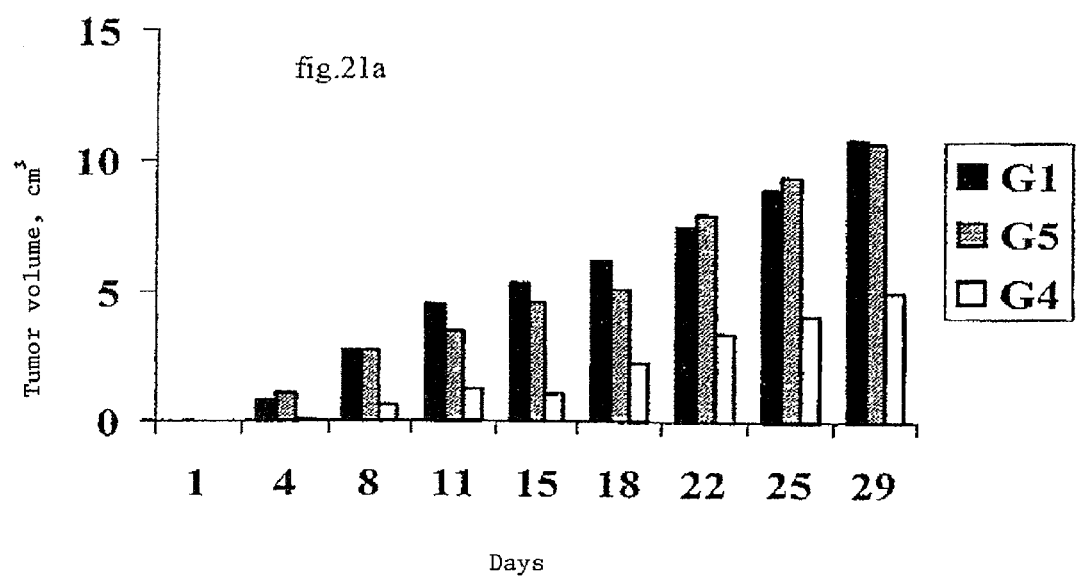
fig.21a
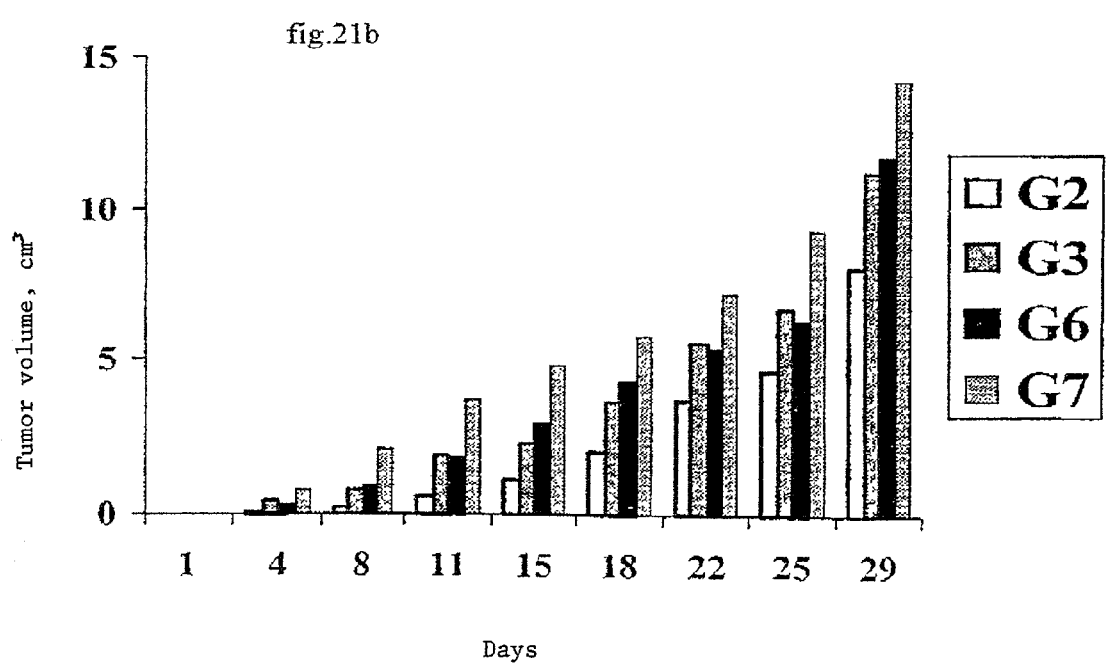
fig.21b

SEQUENCE LISTING

<160> NUMBER OF SEQ ID NOS: 26

<210> SEQ ID NO 1
<211> LENGTH: 29
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(29)
<223> OTHER INFORMATION: Antisense oligonucleotide EF2929AS
<220> FEATURE:
<221> NAME/KEY: modified_base
<222> LOCATION: (1)..(29)
<223> OTHER INFORMATION: Phosphorotioate nucleotide

<400> SEQUENCE: 1
tgagtcataa gaagggttct gctgcccgt                                    29

<210> SEQ ID NO 2
<211> LENGTH: 30
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(30)
<223> OTHER INFORMATION: Oligonucleotide EF 3008AS
<220> FEATURE:
<221> NAME/KEY: modified_base
<222> LOCATION: (12)..(19)
<223> OTHER INFORMATION: Phosphorotioate nucleotide

<400> SEQUENCE: 2
gtagcgaagg gttctgctgc ccgtagctgc                                   30

<210> SEQ ID NO 3
<211> LENGTH: 30
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(30)
<223> OTHER INFORMATION: Control oligonucleotide EF 3008LS
<220> FEATURE:
<221> NAME/KEY: modified_base
<222> LOCATION: (12)..(19)
<223> OTHER INFORMATION: Phosphorotioate nucleotide

<400> SEQUENCE: 3
gtagcgaagg ggtcgtcttc ccgtagctgc                                   30

<210> SEQ ID NO 4
<211> LENGTH: 29
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(29)
<223> OTHER INFORMATION: Control oligonucleotide EF 2929 CS

```
<220> FEATURE:
<221> NAME/KEY: modified_base
<222> LOCATION: (1)..(29)
<223> OTHER INFORMATION: Phosphorotioate nucleotide

<400> SEQUENCE: 4
ctcagcttac tactcagatg atcggctca                                    29

<210> SEQ ID NO 5
<211> LENGTH: 33
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(33)
<223> OTHER INFORMATION: Target sequence D

<400> SEQUENCE: 5
ccagcagaat cgacacatgg cgtgttcaac gct                               33

<210> SEQ ID NO 6
<211> LENGTH: 33
<212> TYPE: RNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(33)
<223> OTHER INFORMATION: Target sequence R

<400> SEQUENCE: 6
ccagcagaau cgacacaugg cguguucaac gcu                               33

<210> SEQ ID NO 7
<211> LENGTH: 21
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(21)
<223> OTHER INFORMATION: Antisense oligonucleotide 21L

<400> SEQUENCE: 7
tgaacacgcc atgtcgattc t                                            21

<210> SEQ ID NO 8
<211> LENGTH: 55
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(55)
<223> OTHER INFORMATION: Antisense oligonucleotide 55L

<400> SEQUENCE: 8
ttactttctt tttgcgttga acacgccatg tcgattcttt ttctttttc ccccc         55

<210> SEQ ID NO 9
```

```
<211> LENGTH: 21
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(21)
<223> OTHER INFORMATION: Antisense oligonucleotide 21PS
<220> FEATURE:
<221> NAME/KEY: modified_base
<222> LOCATION: (1)..(2)
<223> OTHER INFORMATION: Phosphorotioate nucleotide

<400> SEQUENCE: 9
tgaacacgcc atgtcgattc t                                              21

<210> SEQ ID NO 10
<211> LENGTH: 29
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(29)
<223> OTHER INFORMATION: Antisense oligonucleotide H6

<400> SEQUENCE: 10
tgaacacgcc atgtcgattc tttagaatc                                      29

<210> SEQ ID NO 11
<211> LENGTH: 31
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(31)
<223> OTHER INFORMATION: Antisense oligonucleotide H8

<400> SEQUENCE: 11
tgaacacgcc atgtcgattc tttagaatcg a                                   31

<210> SEQ ID NO 12
<211> LENGTH: 33
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(33)
<223> OTHER INFORMATION: Antisense oligonucleotide H10

<400> SEQUENCE: 12
tgaacacgcc atgtcgattc tttagaatcg aca                                 33

<210> SEQ ID NO 13
<211> LENGTH: 37
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
```

```
<221> NAME/KEY: misc_feature
<222> LOCATION: (1)..(37)
<223> OTHER INFORMATION: Antisense oligonucleotide Dh6

<400> SEQUENCE: 13
tgttcatctg aacacgccat gtcgattctt tagaatc                         37

<210> SEQ ID NO 14
<211> LENGTH: 31
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(31)
<223> OTHER INFORMATION: Antisense oligonucleotide L8

<400> SEQUENCE: 14
gcgtatgaac acgccatgtc gattcttacg c                               31

<210> SEQ ID NO 15
<211> LENGTH: 35
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(35)
<223> OTHER INFORMATION: Antisense oligonicleotide L10

<400> SEQUENCE: 15
gcgcttatga acacgccatg tcgattctta agcgc                           35

<210> SEQ ID NO 16
<211> LENGTH: 34
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(34)
<223> OTHER INFORMATION: Phosphodiester oligonucleotide Dh INGFp

<400> SEQUENCE: 16
cagctcttga gctgcacgct gccgtcttga cggc                            34

<210> SEQ ID NO 17
<211> LENGTH: 26
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(26)
<223> OTHER INFORMATION: Phosphodiester oligonucleotide Sh-6 INGFp

<400> SEQUENCE: 17
gagctgcacg ctgccgtctt gacggc                                     26

<210> SEQ ID NO 18
<211> LENGTH: 22
```

```
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(22)
<223> OTHER INFORMATION: Phosphodiester oligonucleotide L4 INGFp

<400> SEQUENCE: 18
gcgagctgca cgctgccgtc gc                                               22

<210> SEQ ID NO 19
<211> LENGTH: 18
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(18)
<223> OTHER INFORMATION: Phosphodiester oligonucleotide L2 ING Fp

<400> SEQUENCE: 19
gagctgcacg ctgccgtc                                                    18

<210> SEQ ID NO 20
<211> LENGTH: 28
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(28)
<223> OTHER INFORMATION: Phosphodiester oligonucleotide L7 INGFp

<400> SEQUENCE: 20
gcgtagagct gcacgctgcc gtctacgc                                         28

<210> SEQ ID NO 21
<211> LENGTH: 28
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(28)
<223> OTHER INFORMATION: Phosphodiester oligonucleotide C7 INGFp
      (negative control)

<400> SEQUENCE: 21
gcgtagagcc gtcacgcgtc gtctacgc                                         28

<210> SEQ ID NO 22
<211> LENGTH: 18
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(18)
<223> OTHER INFORMATION: Oligonucleotide  L2 INGFp
<220> FEATURE:
```

```
<221> NAME/KEY: modified_base
<222> LOCATION: (1)..(2)
<223> OTHER INFORMATION: Phosphorotioate nucleotide
<220> FEATURE:
<221> NAME/KEY: modified_base
<222> LOCATION: (17)..(18)
<223> OTHER INFORMATION: Phosphorotioate nucleotide

<400> SEQUENCE: 22
gagctgcacg ctgccgtc                                                   18

<210> SEQ ID NO 23
<211> LENGTH: 23
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(23)
<223> OTHER INFORMATION: Oligonucleotide L4 INGFp 2S
<220> FEATURE:
<221> NAME/KEY: modified_base
<222> LOCATION: (1)..(2)
<223> OTHER INFORMATION: Phosphorotioate nucleotide
<220> FEATURE:
<221> NAME/KEY: modified_base
<222> LOCATION: (22)..(23)
<223> OTHER INFORMATION: Phosphorotioate nucleotide

<400> SEQUENCE: 23
gcgagctgca cgctgcgcgt cgc                                             23

<210> SEQ ID NO 24
<211> LENGTH: 26
<212> TYPE: DNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_feature
<222> LOCATION: (1)..(26)
<223> OTHER INFORMATION: Oligonucleotide SDh INGFp
<220> FEATURE:
<221> NAME/KEY: modified_base
<222> LOCATION: (1)..(2)
<223> OTHER INFORMATION: Phosphorotioate nucleotide
<220> FEATURE:
<221> NAME/KEY: modified_base
<222> LOCATION: (25)..(26)
<223> OTHER INFORMATION: Phosphorotioate nucleotide

<400> SEQUENCE: 24
gagctgcacg ctgccgtcct cgacgg                                          26

<210> SEQ ID NO 25
<211> LENGTH: 68
<212> TYPE: RNA
<213> ORGANISM: Artificial sequence
<220> FEATURE:
<223> OTHER INFORMATION: Description of the artificial sequence:
      Synthetic oligonucletoide
<220> FEATURE:
<221> NAME/KEY: misc_RNA
<222> LOCATION: (1)..(68)
<223> OTHER INFORMATION: RNA Oligonucleotide EWS FL1-1

<400> SEQUENCE: 25
ucaauauagc caacagagca gcagcuacgg gcagcagaac ccuucuuaug acucagucag     60
```

-continued

```
aagagcag                                                             68

<210> SEQ ID NO 26
<211> LENGTH: 31
<212> TYPE: RNA
<213> ORGANISM: Artificial Sequence
<220> FEATURE:
<223> OTHER INFORMATION: Description of Artificial Sequence:
      Synthetic oligonucleotide

<400> SEQUENCE: 26
ccagcagaau cgacauggcg uguucaacgc u                                   31
```

OLIGONUCLEOTIDES CONTAINING AN ANTISENSE SEQUENCE STABILIZED BY A SECONDARY STRUCTURE, PHARMACEUTICAL COMPOSITIONS CONTAINING THEM AND METHOD OF BLOCKING GENE EXPRESSION USING THEM

RELATED APPLICATION

This is a continuation of International Application No. PCT/FR00/00586, with an international filing date of Mar. 9, 2000, which is based on French Patent Application No. 99/02921, filed Mar. 9, 1999.

FIELD OF THE INVENTION

The present invention pertains to oligonucleotides capable of hybridizing with a target nucleic acid sequence, which oligonucleotides are stabilized by a secondary structure such that they are resistant to degradation in biological media, principally to degradation by nucleases. The invention also pertains to pharmaceutical compositions containing such oligonucleotides and their use to block the in vivo and in vitro expression of genes.

BACKGROUND OF THE INVENTION

Antisense nucleic acids are nucleic sequences capable of hybridizing selectively with target-cell messenger ribonucleic acids (mRNAs) so as to inhibit their translation into protein. These oligonucleotides form double-strand regions with the target mRNA, in a local manner, by interaction of the classic Watson-Crick type.

Many pathological states are the consequence of the expression of an abnormal gene within a cell. Such foreign genes can be integrated in the cellular deoxyribonucleic acid (DNA), for example, by a viral infection, and can therefore be expressed by the cell. The same is true for numerous oncogenes which are capable of conferring a cancerous phenotype to a eukaryotic cell, thus resulting in a tumor in an entire organism.

One approach proposed for inhibiting the action of such genes is based on the use of antisense oligonucleotides [1–3]. Indeed, the regulation of the expression of target genes by means of antisense oligonucleotides constitutes a therapeutic approach in the early stages of development. This approach depends on the capacity of the oligonucleotides to hybridize specifically at complementary regions of a nucleic acid and to thereby inhibit specifically the expression of target genes. This inhibition can take place either at the translational level by an antisense oligonucleotide or at the transcriptional level by an antigene oligonucleotide.

The therapeutic application of antisense technology has been extensively investigated in numerous viral infections, including the acquired immunodeficiency virus [4], the influenza virus [5], the Epstein-Barr virus [6], human papillomaviruses [7, 8] and the herpes simplex virus [9, 10].

It can be a question, for example, of synthetic oligonucleotides of small size, complementary to cellular mRNA, which are introduced into the target cells. Such oligonucleotides have been described, e.g., in European Patent Application No. 92 574. It can also be a question of antisense genes whose expression in the target cell generates RNA complementary of cellular mRNA. Such genes have been described, e.g., in European Patent Application No. 140 308.

Nevertheless, the in vivo use of antisense nucleic acids has encountered a number of difficulties which have, to date, limited their therapeutic exploitation.

In fact, nucleic acids exhibit a high degree of sensitivity to degradation by the enzymes of the organism, such as the nucleases [11, 12], which necessitates the use of high doses. Moreover, they exhibit weak penetration into certain cell types and an intracellular distribution which is often inadequate, both of which can render them deficient in therapeutic effect. Additionally, it is important to have available sequences that are sufficiently selective and stable so as to obtain a specific effect without altering other cell functions.

Since the first attempts by Stephenson and Zamecnik [13] to inhibit the Rous sarcoma virus using phosphodiester oligonucleotides, numerous efforts have been made to optimize the efficacy of these oligonucleotides, notably with regard to their cellular penetration [14–16], attachment to their target [17] and resistance to nucleases [18–20].

Insufficient resistance of oligonucleotides to nucleases remains a problem that limits the developmental possibilities of this therapeutic strategy. As an attempt to resolve this problem, it has been proposed to chemically modify the phosphodiester skeleton of the nucleic acids so as to create new classes of artificial oligonucleotides [21–23]. Among these modified oligonucleotides are phosphonate, phosphoramidate and phosphorothioate oligonucleotides which are described, e.g., in International Patent Application PCT No. WO 94/08003, or oligonucleotides coupled to different agents such as cholesterol, a peptide, a cationic polymer, etc.

Although certain of these modified oligonucleotides exhibit good resistance to nucleases, these modifications can have the drawback of being accompanied by the loss of other properties which are important for the antisense activity, such as their affinity for the RNA targets, their capacity to modulate the degradation of RNAs by RNases, and their power of penetration and distribution in the cell compartments remain very weak [1, 22, 24]. Furthermore, their biological activity is not always increased and they can exhibit certain secondary effects linked to the presence of non-natural motifs in their structure. In fact, the oligonucleotides modified in this manner exhibit certain undesirable characteristics such as nonspecific interactions with cellular proteins and a high level of cytotoxicity [25–29].

Another method enabling increased resistance of the oligonucleotides to nucleases but using natural phosphodiesters consists of grafting on the 3' end of the sequence to be protected a dodecanol conjugate (European Patent Applications No. EP 117 777 and No. EP 169 787).

In order to resolve the previously mentioned drawbacks, it has also been proposed in International Patent Application PCT No. WO 94/12633, to add to one and/or both ends of the antisense sequence to be protected nucleotide sequences whose secondary structure is presented in the form of loops or hairpins, capable of preventing the nucleases from degrading the antisense sequence [30–35]. However, this technique is not satisfactory because the presence of the supplementary nucleotides of the hairpin sequences impedes the hybridization of the antisense sequence with the target nucleic acids.

BRIEF SUMMARY OF THE INVENTION

This invention offers new oligonucleotides capable of modifying or inhibiting the in vivo or in vitro expression of genes and which are resistant to nuclease digestion but without having the drawbacks described above. This invention is attained by means of an oligonucleotide containing at least one secondary structure and capable of modifying or inhibiting the in vivo or in vitro expression of a target gene, characterized in that it comprises an antisense sequence and possibly a supplementary nucleotide sequence at one and/or both ends of the antisense sequence, selected in a manner such that the secondary structure(s) disintegrates upon attachment of the oligonucleotide to the target nucleic acid.

Thus, the oligonucleotides of the invention comprise at least two regions substantially complementary to each other forming the secondary structure, with each of said regions belonging in part or totally to the antisense sequence.

BRIEF DESCRIPTION OF THE DRAWINGS

FIG. 7 represents the oligonucleotides used in Example 1. The 21-mer DNA (D) (SEQ. ID. NO. 5) and RNA (R) (SEQ. ID. NO. 6) target sequences are underlined. The sequences of the antisense oligodeoxyribonucleotides complementary to the D and R targets are also shown.

FIG. 8 represents the electrophoresis analysis of the formation of 15% native PAGE duplexes at 37° C.

FIG. 11 represents the degradation of the antisense oligonucleotides in cell lysates: (a, b) lysate HeLa, (c, d) lysate NIH 3T3.

FIG. 12 represents the degradation of the antisense oligonucleotides complexed with SuperFect™ inside the cells: (a, b) lysate HeLa, (c, d) lysate NIH 3T3.

FIG. 13 represents the oligonucleotides used in Example 2.

FIG. 15A illustrates the secondary structure of EF 2929AS (SEQ. ID. NO. 1).

FIG. 15B shows the interaction of EP 2929AS (SEQ. ID. NO. 1) with the target EWS-Fli1 RNA (SEQ. ID. NO. 25).

FIG. 16A illustrates the secondary structure of a second antisense oligonucleotide analyzed in Example 3, EF 3008AS (SEQ. ID. NO. 2).

FIG. 16B shows the interaction of EF 3008AS (SEQ. ID. NO. 2) with the target EWS-Fli1 RNA (SEQ. ID. NO. 25).

FIG. 17 shows the sequences of oligonucleotides EF 2929AS (SEQ. ID. NO. 1) and EF 3008AS (SEQ. ID. NO. 2).

FIG. 18A illustrates analysis of the degradation of oligonucleotide EF 3008AS (SEQ. ID. NO. 2) in culture medium containing NCS or MH.

FIG. 18B illustrates analysis of the degradation of oligonucleotide EF 2929AS (SEQ. ID. NO.1) in culture medium containing NCS or MH.

FIGS. 20 and 21 represent evaluation of tumoral volume of male nude mice aged 6 weeks with or without oligonucleotides of the invention.

DETAILED DESCRIPTION OF THE INVENTION

The oligonucleotides of the invention comprise at least two regions substantially complementary to each other forming the secondary structure, with each of said regions belonging in part or totally to the antisense sequence.

The term "substantially complementary" is understood to mean that said regions can contain some mispairings, said mispairing involving advantageously less than half of the nucleotides of said regions of the oligonucleotides of the invention.

The oligonucleotides according to the invention are remarkable in that they are constituted by a sequence which gives it a structure capable of disintegrating upon attachment of the oligonucleotide to its target. The oligonucleotides according to the invention are thus especially advantageous compared to the oligonucleotides with a secondary structure of the prior art because they make it possible for the same oligonucleotide length to have available a greater length attached to the target which assures greater stability of the hybrid. Furthermore, in contrast to the prior art, the secondary structure of the oligonucleotides according to the invention disintegrates upon hybridization and therefore does not impede the attachment of the antisense sequence to its target.

In the context of the present invention, the term "secondary structure" is a understood to mean a hairpin, loop or spiral structure in which the single-stranded or double-stranded oligonucleotide is open, i.e., its 3' and 5' ends are free. The invention pertains more specifically to a hairpin secondary structure.

Various modes of implementation can be envisaged for the oligonucleotides of the invention depending on whether the secondary structure is formed:
  essentially from part or all of the antisense sequence,
  essentially from part or all of the supplementary nucleotide sequences situated on either side of the antisense sequence, from part or all of the antisense sequence and from part or all of one or both of the two supplementary sequences situated on either side of said antisense sequence.

PREFERRED EMBODIMENTS

Figure 1:
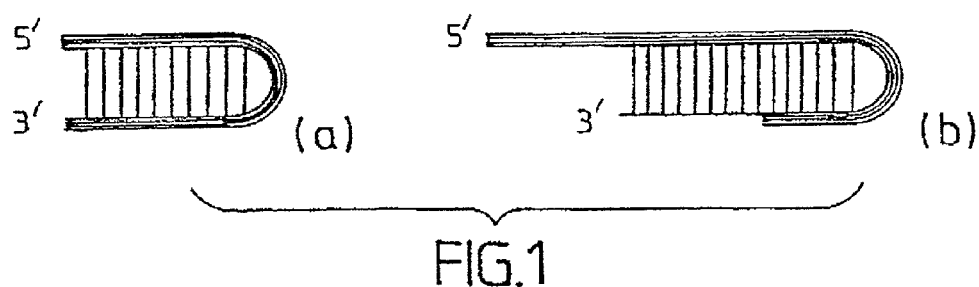
FIG. 1a illustrates an example of the invention wherein the secondary structure of the oligonucleotide is formed exclusively of nucleotide pairs belonging to the antisense sequence.
FIG. 1b illustrates an example of the invention wherein the secondary structure of the oligonucleotide is formed principally of nucleotide pairs belonging to the antisense sequence.

According to a first form of implementation of an oligonucleotide according to the invention, the secondary structure is formed principally or exclusively of nucleotide pairs belonging to the antisense sequence. An example of an oligonucleotide of this type is shown in attached FIG. 1. Thus, this form of implementation pertains to target nucleic acids possessing pseudopalindromic sequences that are estimated to be approximately 2% of the human genome. This mode of implementation of the invention offers the advantage that, upon attachment of the antisense oligonucleotide to its target, no free unpaired strand is left which could:
  be accessible to exonucleases,
  interfere with other DNA sequences close to the target.

Figure 2:
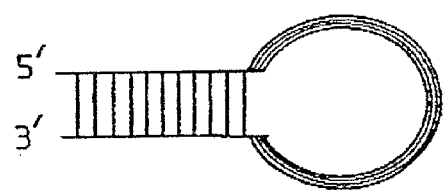
FIG. 2 illustrates an example of the invention wherein the secondary structure of the oligonucleotide is formed essentially or exclusively of nucleotide pairs belonging to supplementary nucleotide sequences situated at the 5' and 3' ends of the antisense sequence.
Figure 3:
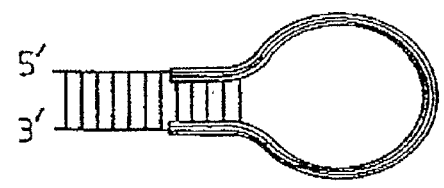
FIG. 3 illustrates an example of the invention wherein the secondary structure of the oligonucleotide is formed essentially or exclusively of nucleotide pairs belonging to supplementary nucleotide sequences situated at the 5' and 3' ends of the antisense sequence and to one or more nucleotide pairs belonging exclusively to the antisense sequence.

According to a second form of implementation of an oligonucleotide according to the invention, the secondary structure is formed essentially or exclusively of nucleotide pairs belonging to the supplementary nucleotide sequences situated at the ends of the antisense sequence. In this form of implementation, the nucleotide sequences located on either side of the antisense sequence are therefore substantially complementary. An example of an oligonucleotide of this type is shown in attached FIG. 2. In this mode of implementation, it is also possible that the secondary structure also comprises one or more nucleotide pairs belonging exclusively to the antisense sequence as shown in FIG. 3.

Figure 4:
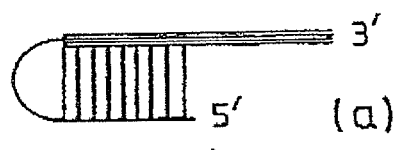
FIG. 4a illustrates an example of the invention wherein the secondary structure of the oligonucleotide is formed from nucleotide pairs belonging to the antisense sequence and to a supplementary nucleotide sequence located at the 5' end of the antisense sequence and wherein the supplementary nucleotide sequence is substantially complementary to the antisense sequence.
FIG. 4b shows an example of the invention as in FIG. 4a wherein the secondary structure comprises one or more nucleotide pairs belonging exclusively to the antisense sequence.
Figure 5:
FIG. 5 illustrates an example of the invention wherein the secondary structure of the oligonucleotide is formed from nucleotide pairs between the antisense sequence and a supplementary nucleotide sequence located at the 3' end of the antisense sequence and wherein the supplementary nucleotide sequence is substantially complementary to the antisense sequence.
Figure 6:
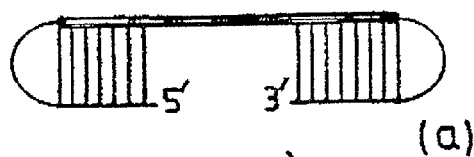
FIG. 6a illustrates an example of the invention wherein the two secondary structures of the oligonucleotide are formed from nucleotide pairs belonging to the antisense sequence and to supplementary nucleotide sequences located at the 5' and 3' ends of the antisense sequence and wherein the supplementary nucleotide sequences located at the 5' and 3' ends of the antisense sequences are substantially complementary to the antisense sequence.
FIG. 6b shows an example of the invention as in FIG. 6a wherein the secondary structures comprise one or more nucleotide pairs belonging exclusively to the antisense sequence.

According to a third form of implementation of an oligonucleotide according to the invention, the secondary structure is formed by nucleotide pairs belonging to the antisense sequence and to a supplementary nucleotide sequence located at one of the ends of said antisense sequence. In this form of implementation, the nucleotide sequence located at one of the ends of the antisense sequence is substantially complementary to said antisense sequence. It is understood, of course, that in this mode of implementation the oligonucleotide can comprise two secondary structures, one at each end of the antisense sequence. An example of an oligonucleotide of this type is shown in attached FIGS. 4, 5 and 6. In this mode of implementation, it is also possible that the secondary structure comprises one or more nucleotide pairs belonging exclusively to the antisense sequence.

In these three modes of implementation of the oligonucleotides of the invention, the one or two secondary structure(s) disintegrate upon attachment of the oligonucleotide to its target. In the cases in which the oligonucleotide of the invention comprises one or two supplementary nucleotide sequences, these sequences, upon attachment of the antisense sequence to the target remain in a simple strand form and do not impede the stability of the hybrid or the attachment of the RNase H to this hybrid. This is very important because it is the RNase H which is the final cause of the antisense effect. In fact, it is precisely one of the drawbacks of the oligonucleotides of the prior art with secondary structures that they do not disintegrate upon attachment of the antisense sequence to its target.

The secondary structure present in the oligonucleotides of the invention comprises from three to twenty pairs of successive nucleotides but can also include several mispairings as long as they do not modify substantially the stability of the secondary structure. The secondary structure preferably present in the oligonucleotides of the invention comprises from five to ten nucleotide pairs.

The oligonucleotides of the invention are preferably constituted by DNA. In fact, since a DNA/DNA hybrid is less stable than a DNA/RNA hybrid, close to the target nucleic acid the secondary structure of the oligonucleotides of the invention disintegrates to the benefit of the formation of the hybrid formed by the antisense sequence and the target without subsequent reformation of the secondary structure.

The oligonucleotides of the invention resist degradation in biological media without requiring the use of chemically modified nucleotides or coupling to the various chemical groups or compounds described in the prior art. They are thus constituted by natural nucleotides which are advantageously less expensive than chemically modified nucleotides and which avoid the drawback associated with chemically modified nucleotides of generating degradation products that are toxic to the cells. Nevertheless, for example, for in vitro uses or to accumulate the protective effects against degradation due, on the one hand, to the secondary structure and, on the other hand, to chemical modifications, the oligonucleotides of the invention can be constituted by or contain chemically modified bases or be coupled to various agents known in the field. Thus, in certain modes of implementation the antisense oligonucleotides of the invention can contain one or more modified nucleotide(s) of the phosphonate, phosphoramidate and phosphorothioate type. These modified nucleotides advantageously form the 3' and 5' ends of an oligonucleotide whose secondary structure is formed principally or exclusively of nucleotide pairs belonging to the antisense sequence, and whose 3' and 5' ends are preferably paired.

The antisense sequence constituting the oligonucleotides of the invention comprises on the order of 5 to 30 nucleotides and preferably on the order of 8 to 20 nucleotides.

The invention also pertains to the pharmaceutical compositions containing one or more of the previously described oligonucleotides, which may be identical or different, associated in said composition with a pharmaceutically acceptable vehicle. The oligonucleotides of the invention may be free, encapsulated, coupled, conjugated to various substances such as antibodies, proteins, liposomes, microspheres, microorganisms or cells suitable to the modes of administration employed, or to any other type of vector such as nanoparticles, dendrimers, cationic lipids or peptides.

A pharmaceutical composition according to the invention for the treatment of Ewing's sarcoma is characterized in that it comprises as active principle at least one of the oligonucleotides shown in the sequence listing as numbers SEQ. ID. NO. 1 or SEQ. ID. NO. 2.

The oligonucleotides of the invention are intended especially for hybridization with a complementary mRNA sequence and can be used as drugs for the treatment of a human, animal or plant organism, said treatment consisting of blocking the expression of one or more genes implicated in the targeted pathology. But the oligonucleotides of the invention can also be used in the field of diagnostics in relation to the problem of resistance of the oligonucleotides in a biological medium, such as, e.g., genetic screening of biological material with labeled probes.

Other advantages and characteristics of the invention will be perceived from the examples below and FIGS. 1 to 6 which represent schematically the examples of implementation of the oligonucleotides of the invention. In these figures, the thick lines represent the antisense sequence, the thin lines represent the supplementary sequence(s) if such is present and the vertical bars therebetween represent the bonds of the base pairs. The Examples are presented as nonlimiting examples.

EXAMPLES

Example 1

Study of Antisense Oligonucleotides of the Invention Comprising a Region Complementary of the env RNA Translation Initiation Region of the Friend Murine Leukemia Retrovirus I—Materials and Methods 1) Oligonucleotides The oligonucleotides were acquired from the Eurogentec company (Seraing, Belgium) then desalted on Sephadex G25 columns and quantified by absorbance at 260 nm.

2) Protection of the Phosphate 5' End of the Antisense Oligonucleotides

The labeling at the 5' end of the oligonucleotides was performed using ($^{32}$P-γ)ATP (Amersham) and T4 polynucleotide kinase (Promega). The labeled oligonucleotides were then purified by electrophoresis on a 20% denaturing polyacrylamide gel, then dissolved in 100 µl of a buffer of 1M N-methylmorphine, 20 mM MgCl$_2$ (pH 7.5) containing 50% ethanol and the solution was supplemented by 10 mg of 1-ethyl-3(3'-dimethylamino propyl)carbodiimide. The reaction was performed for 16 hours at 4° C. and the oligo nucleotides were precipitated twice with 1 ml of a 2% solution of LiClO$_4$ in acetone and washed with acetone. These oligonucleotides having the terminal phosphate protected by an ethyl residue against hydrolysis by a phosphatase were then mixed with unlabeled oligodeoxynucleotides and used to study their resistance to enzymatic digestion.

3) Thermal Denaturation Experiments

The absorbance/temperature curves were recorded at 260 nm using a Uvikon 933 spectrophotometer equipped with a thermoprogrammer. The oligodeoxynucleotide solutions were prepared in 600 µl of 10 mM sodium phosphate buffer (pH 7.5) with 50 mM NaCl. The concentration of each oligonucleotide strand was $10^{-6}$ M. The absorbance was measured while the temperature was increased from 20° C. to 80° C. at the rate of 0.5° C. per minute. The melting points ($T_m$) were determined by data processing adjustment from the first derivative of the absorbance according to 1/T. The precision of the $T_m$ values were estimated at ±0.5° C. from repetitions of the experiments. The free energy values for the dissociation of the duplex was derived by data processing adjustment of the melting curves using the two-state model [35].

4) Native Gel Electrophoresis

The RNA and DNA matrices (R and D) were labeled using ATP($^{32}$P-γ) and the T4 polynucleotide kinase. The oligonucleotides (10 pmoles for each strand) were dissolved in 10 µl of 20 mM Tris-acetate, 150 mM CH$_3$COONa, 2 mM MgCl$_2$ buffer (pH 7.5) and incubated at 37° C. for 1 hour then supplemented with 1 µl of a 70% solution of glycerol containing xylene cyanol and bromophenol blue. The electrophoreses were performed in a non-denaturing 15% acrylamide gel (19:1 acrylamide/bis-acrylamide) in the same Tris-acetate buffer at 37° C. for 24 hours (9 V/cm).

5) Cleavage by RNase H

In order to investigate the triggering of RNase H activity by the oligodeoxynucleotides, 10 pmoles of the oligodeoxynucleotides were mixed with 1 pmole of the RNA matrix (R) labeled at 5' with ($^{32}$P) in 10 µl of 20 mM Tris-HCl, 10 mM MgCl$_2$, 100 mM KCl, 0.1 mM DTT buffer (pH 7.5) in the presence of 0.5 µl of RNasin (Gibco BRL) and incubated for 30 minutes at 37° C. Then 0.5 U of *E. coli* RNase H (Promega, Madison, Wis.) was added and the mixtures were incubated at 37° C. for 15 minutes. The samples were precipitated with acetone containing 2% LiClO$_4$, dried, dissolved in 4 µl of formamide:water (4:1), 0.01% of bromophenol blue and 0.01% of xylene cyanol and analyzed by electrophoresis in a 20% denaturing polyacrylamide gel, followed by autoradiography.

6) Cells and Media

Cells lines NIH 3T3 and HeLa were cultured in a DMEM medium supplemented with 5 and 10%, respectively, of heat-inactivated fetal bovine serum (FBS) (Gibco, BRL), streptomycin (100 mg/µl) and penicillin (100 U/ml). All of the cells were incubated at 37° C. in 5% CO$_2$.

7) Preparation of the Cell Lysates

The NIH 3T3 and HeLa cells were washed three times with PBS then deposited in 1 ml of 10 mM sodium phosphate, 10 mM MgCl$_2$, 150 mM NaCl, 1 mM DTT, 1% NP-40, 02 mg/ml phenylmethyl sulphonyl fluoride (PMSF) buffer (pH 7.5) and stored at −20° C. for 30 minutes. After thawing, the cells were centrifuged at 14,000 g for 15 minutes at 4° C. The supernatant was used to study the enzymatic degradation of the oligonucleotides. The protein concentration of each lysate was quantified using bovine serum albumin (BSA) as standard [37].

8) Study of the Degradation of the Oligonucleotide in a Biological Medium

Determination of the degree of degradation of the oligonucleotides was performed in DMEM containing 10% heat-inactivated FBS (56° C. for 30 minutes) and in the cell lysates. The lysates were diluted in a 10 mM sodium phosphate, 10 mM MgCl$_2$, 150 mM NaCl, 1 mM buffer (pH 7.5) so as to have available the same total concentration of protein of 1.22 mg/ml. In order to avoid enzymatic cleavage of the $^{32}$P-labeled phosphate, oligonucleotides with the protected terminal phosphate prepared as described above were used. Oligodeoxynucleotides labeled with $^{32}$P at a concentration of 10 μM were incubated in 120 μl of the corresponding medium at 37° C. At different times, 15-μl aliquots were collected as samples, supplemented by 15 μl of 50 mM EDTA and frozen at −20° C. The samples were extracted twice with a phenol/chloroform/iso-amyl alcohol mixture (25/24/1). The oligonucleotides were precipitated from the aqueous fractions by 10 volumes of acetone containing 2% LiClO$_4$, dried and dissolved in 5 μl of a formamide/water mixture (4/1), 0.01% bromophenol blue and 0.01% xylene cyanol. The samples were analyzed by electrophoresis on a 20% denaturing polyacrylamide gel. The resultant gels were scanned using a phosphorimager (Storm 840, Molecular Dynamics). The degradation of the oligonucleotides was quantified as the ratio of the effective signal of the bands corresponding to the intact and degraded oligonucleotides. The precision of the percentage degradation was estimated at ±0.5% on the basis of repetitions of the experiments.

9) Study of the Degradation of the Oligonucleotide in the Cell

One day earlier, the cells were grown on a 6-well plate so as to obtain 60–80% confluence (4×10$^5$ cells). 5 μg of each oligodeoxynucleotide was mixed with 6 μl of SuperFect™ (Qiagen, Canada) in a final volume of 150 μl of DMEM (without FBS or antibiotic) for 10 minutes at room temperature. The cells were washed with PBS, the SuperFect™-oligodeoxynucleotide mixtures were diluted with 850 μl of 10% (for the HeLa cells) or 5% (for the NIH 3T3 cells) FBS DMEM (with the antibiotics) and added to the cells.

The supernatant was extracted after 16 or 48 hours and the cells were collected by a trypsin treatment. The cells were then washed three times with PBS, suspended in 500 μl of 10 mM sodium phosphate, 150 mM NaCl, 20 mM EDTA, 1% NP-40 buffer (pH 7.5) and allowed to stand for 30 minutes at −20° C. After thawing, the cells were heated for 30 minutes at 90° C. in order to completely destroy all of the cellular compartments and extracted twice with a phenol/chloroform/iso-amyl alcohol mixture (25/24/1). The oligodeoxynucleotides were precipitated from aqueous fractions containing 0.5 M sodium acetate by adding a fivefold excess of ethanol dissolved in a formamide/water mixture (4/1), 0.01% bromophenol blue and 0.01% of xylene cyanol, and analyzed by electrophoresis on 20% denaturing gel. The resultant gels were scanned using a phosphorimager (Storm 840, Molecular Dynamics). The degradation of the oligonucleotides was quantified as the ratio of the effective signal of the bands corresponding to the intact and degraded oligonucleotides.

II—Results

1) Structures of the Structured Oligonucleotides

As shown in FIG. 7, all of the oligodeoxyribonucleotides studied contained the 21-base sequence 5'-TGAACACGC-CATGTCGATTCT-3' (SEQ. ID. NO. 7), shown in FIG. 7, complementary to the env RNA translation initiation region of the Friend murine leukemia retrovirus. The 21L (SEQ. ID. NO. 7) and 55L (SEQ. ID. NO. 8) oligonucleotides have a linear structure like the 21PS (SEQ. ID. NO. 9) oligonucleotide. However, the 21PS (SEQ. ID. NO. 9) oligonucleotide contains two phosphorothioate groups at each end to protect it from enzymatic degradation. The H6 (SEQ. ID. NO. 10), H8 (SEQ. ID. NO. 11) and H10 (SEQ. ID. NO. 12) oligonucleotides present a different number of base pairs (bp) in the supplementary sequence of the hairpin secondary structure located at the 3' end. Dh6 (SEQ. ID. NO. 13) can form a hairpin secondary structure with the 6-bp tails at the 5' and 3' ends. L8 (SEQ. ID. NO. 14) and L10 (SEQ. ID. NO. 15) can form loop secondary structures with 13 nucleotides situated in the loop and in the tails with 8 and 10 base pairs, respectively.

2) Study of the Binding Properties of the Oligonucleotides

Table 1 below shows the melting point ($T_m$) and the $\Delta G^0_{37}$ determined both for the oligonucleotides alone and for the complexes with the target DNA (D) (SEQ. ID. NO. 5) or RNA (R) (SEQ. ID. NO. 6), 50 mM NaCl, pH=7.5.

TABLE 1

| oligonucleotide + target | $T_m^{(a)}$ (° C.) | $-\Delta H^{(b)}$ (kcal mol$^{-1}$) | $-\Delta S^{(c)}$ (e.u.) | $-\Delta G^0_{37}$ (kcal mol$^{-1}$) |
|---|---|---|---|---|
| 21L + D | 60 | 101 | 267 | 18.2 |
| 21L + R | 57 | 105 | 286 | 16.3 |
| 21PS + D | 60 | 82 | 215 | 15.4 |
| 21PS + R | 57 | 86 | 232 | 14.1 |
| H6 | 52 | 45 | 139 | 1.9 |
| H6 + D | 58 | 92 | 249 | 14.8 |
| H6 + R | 56 | 82 | 222 | 13.2 |
| H8 | 66 | 62 | 190 | 3.1 |
| H8 + D | 60 | 60 | 151 | 13.2 |
| H8 + R | 56 | 52 | 130 | 11.7 |
| H10 | 75, | 44 | 128 | 4.3 |
| H10 + D | 43, 60, 73 | 43 | 102 | 11.4 |
| H10 + R | 40, 57, 73 | 35 | 78 | 10.8 |
| Dh6 | 52 | 35 | 104 | 2.8 |
| Dh6 + D | 57 | 90 | 245 | 14.1 |
| Dh6 + R | 55 | 80 | 218 | 12.4 |
| L8 | 47 | 46 | 142 | 2.0 |
| L8 + D | 60 | 96 | 260 | 15.4 |
| L8 + R | 57 | 101 | 280 | 14.2 |
| L10 | 53 | 68 | 208 | 3.5 |
| L10 + D | 57 | 94 | 255 | 15.0 |
| L10 + R | 55 | 96 | 265 | 13.9 |

ΔH, ΔS and ΔG are the means of multiple values obtained from independent melting curves and are rounded off.
$^{(a)}$the error on the values of $T_m$ is ± 0.5° C.
$^{(b)}$the error on the values of ΔH is ± 5 kcal mol$^{-1}$.
$^{(c)}$the error on the values of ΔS is ± 10 e.u.

The double-stranded domains of the oligodeoxynucleotides with secondary structures, designated as "structured oligodeoxynucleotides," were found to be stable under essentially physiological conditions. The thermal stability of the internal duplexes of oligodeoxynucleotides H6 (SEQ. ID. NO. 10), H8 (SEQ. ID. NO. 11), H10 (SEQ. ID. NO. 12) AND L8 (SEQ. ID. NO. 14) and L10 (SEQ. ID. NO. 15) depends on the number of base pairs in their tail region. However, as shown in Table 1, all of the structured oligodeoxynucleotides are capable of interacting with both DNA and RNA targets to form intermolecular duplexes having thermodynamic parameters that are different from the intramolecular duplexes. The $T_m$ values found for these bimolecular duplexes differ significantly from the $T_m$ values of the structured oligodeoxynucleotides and correspond approximately to the $T_m$ values detected for the duplexes formed by the linear oligodeoxynucleotide 21 L (SEQ. ID. No. 7) with the two targets. The only exception is the oligonucleotide H10 (SEQ. ID. NO. 12) which presents a very stable hairpin ($T_m$=75° C.). In the presence of D (SEQ. ID. NO. 5) or R (SEQ. ID. NO. 6) targets, the melting point curve presents three periods:

the first corresponds to the melting point of a partial intermolecular duplex formed between the 11-mer single-stranded fragment of this oligodeoxynucleotide and the target (43° C. with the DNA target and 40° C. with the RNA target), the second corresponds to the melting point of the complete intermolecular duplex (60° C. with the DNA target and 57° C. with the RNA target), the third corresponds to the melting point of its own double-stranded domain (73° C.).

Figure 8A:
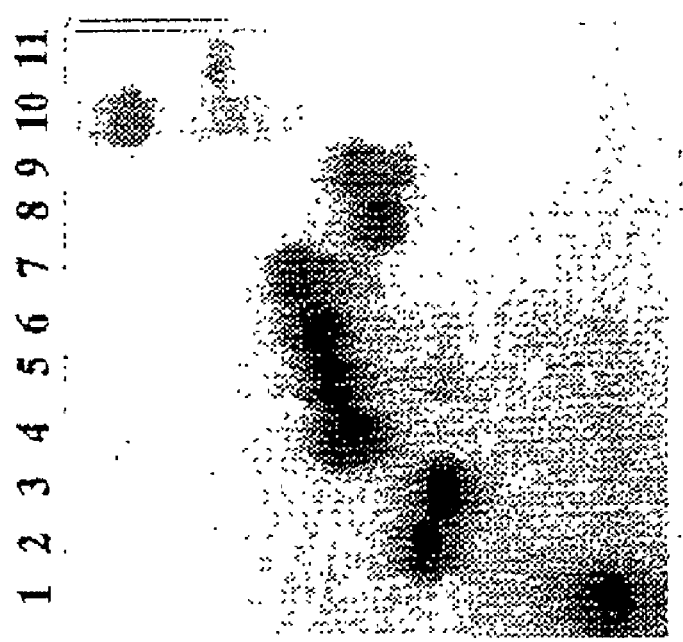
FIG. 8a demonstrates attachment of the $^{32}$P-labeled target RNA (line 1) to the oligodeoxynucleotides 21L (SEQ. ID. NO. 7) (line 2), 21PS (SEQ. ID. NO. 9) (line 3), H6 (SEQ. ID. NO. 10) (line 4), H8 (SEQ. ID. NO. 11) (line 5), H10 (SEQ. ID. NO. 12) (line 6), Dh6 (SEQ. ID. NO. 13) (line 7), L8 (SEQ. ID. NO. 14) (line 8), L10 (SEQ. ID. NO. 15) (line 9), SL (line 10), 55L (SEQ. ID. NO. 8) (line 11).
Figure 8B:
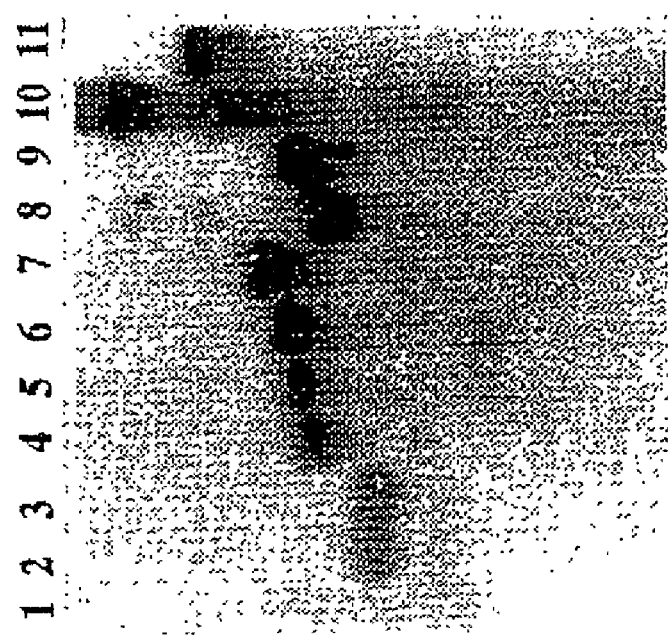
FIG. 8b demonstrates attachment of the $^{32}$P-labeled target DNA (line 1) to the oligodeoxynucleotides 21L (SEQ. ID. NO. 7) (line 2), 21PS (SEQ. ID. NO. 9) (line 3), H6 (SEQ. ID. NO. 10) (line 4), H8 (SEQ. ID. NO. 11) (line 5), H10 (SEQ. ID. NO. 12) (line 6), Dh6 (SEQ. ID. NO. 13) (line 7), L8 (SEQ. ID. NO. 14) (line 8), L10 (SEQ. ID. NO. 15) (line 9), SL (line 10), 55L (SEQ. ID. NO. 8) (line 11).

The attachment of the structured oligodeoxynucleotides to the DNA and RNA targets was also studied using a gel mobility test. The oligodeoxynucleotides were incubated with D (SEQ. ID. NO. 5) and R (SEQ. ID. NO. 6) targets labeled with ($^{32}$P) at 37° C. and the mobility of the complexes formed was determined by electrophoresis in a non-denaturing 15% polyacrylamide gel. FIG. 8 shows that the electrophoretic mobility of both targets changes in the presence of all of the structured oligodeoxynucleotides due to their involvement in the formation of the corresponding complexes.

Figure 9:
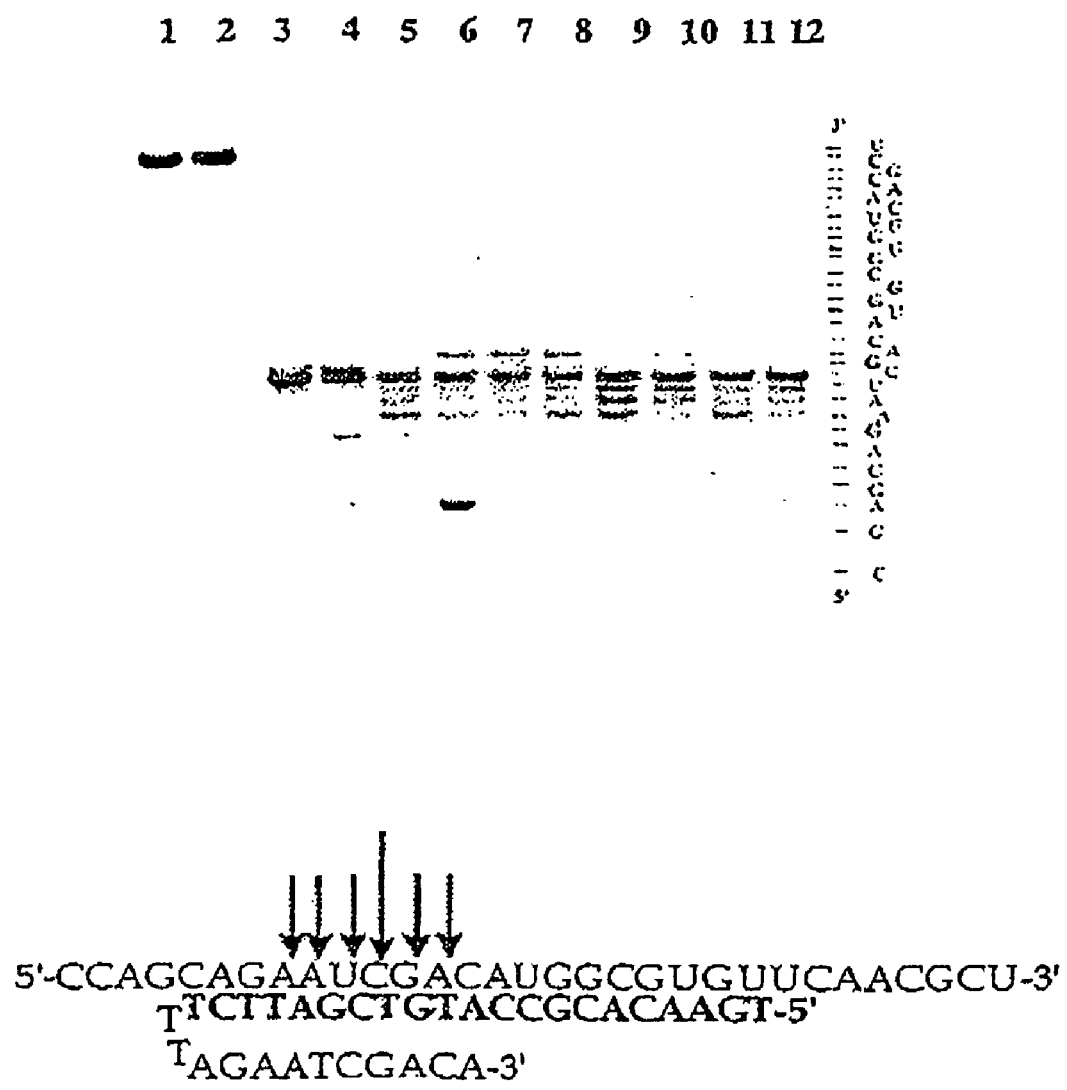
FIG. 9 represents the cleavage of the RNA target by RNase H in the presence of the antisense oligonucleotides 21L (SEQ. ID. NO. 7) (line 2), 21PS (SEQ. ID. NO. 9) (line 3), H6 (SEQ. ID. NO. 10) (line 4), H8 (SEQ. ID. NO. 11) (line 5), H10 (SEQ. ID. NO. 12) (line 6), Dh6 (SEQ. ID. NO. 13) (line 7), L8 (SEQ. ID. NO. 14) (line 8), L10 (SEQ. ID. NO. 15) (line 9), SL (line 10), 55L (SEQ. ID. NO. 8) (line 11). $^{32}$P-labeled RNA R (SEQ. ID. NO. 6) alone (line 1) and in the presence of RNase H without oligodeoxynucleotides (line 12). The arrows indicate the major cleavage sites.

The capacity of the structured oligodeoxynucleotides to hybridize to the complementary RNA strand and to trigger cleavage by RNase was also studied. FIG. 9 shows the result of the incubation of the RNA target (0.1 µM) and different oligodeoxynucleotides (1 µM) with 0.5 unit of RNase H for 15 minutes at 37° C. Cleavage of the RNA (R) (SEQ. ID. NO. 6) by RNase H in the presence of the linear oligonucleotide 21L (SEQ. ID. NO. 7) and of all of the structured oligodeoxynucleotides took place with the same efficacy and at the same sites. The major cleavage sites are indicated by arrows in FIG. 9. In the absence of complementary oligodeoxynucleotides, no cleavage of the RNA was seen.

All of these results demonstrate that the internal double-stranded structure of the oligodeoxynucleotides does not impede their interaction with their DNA or RNA targets. The internal duplexes appear to dissociate when the bimolecular complexes between the structured oligonucleotides and their targets are formed. Evidently, as shown in Table 1, the bimolecular duplexes are thermodynamically preferred.

3) Stability of the Antisense Oligonucleotides in Relation to Nucleolytic Degradation The capacity of the oligodeoxynucleotides with a secondary structure to resist enzymatic hydrolysis was studied in DMEM supplemented with 10% of heat-inactivated FBS, generally used for cell growth, as well as in the cellular lysates of two types of cell lines (NIH 3T3 and HeLa). So as to avoid cleavage of the phosphate labeled with ($^{32}$P), oligonucleotides with a 5'-end phosphate protected by an ethyl residue were used for this study.

Figure 10:
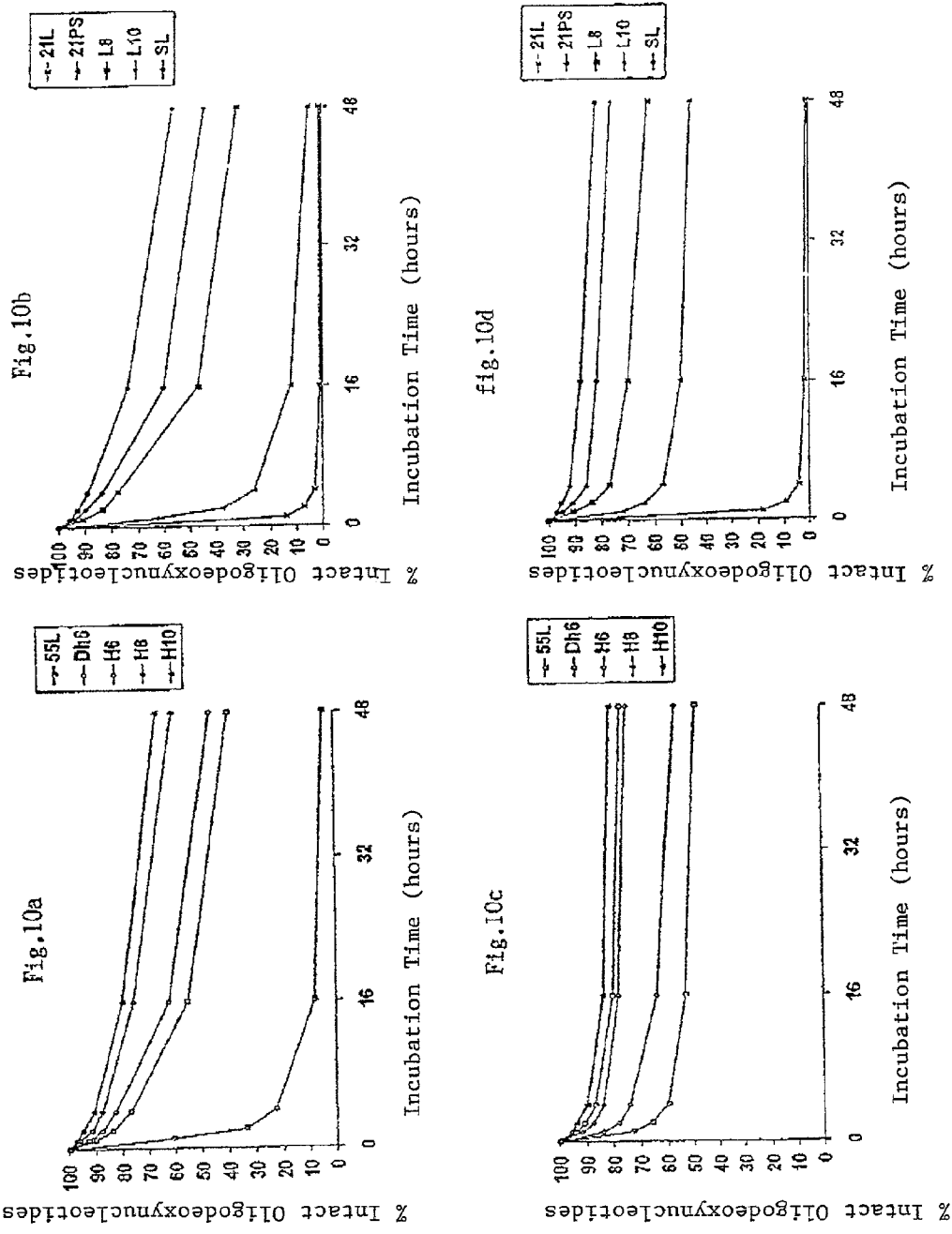
FIG. 10 represents the degradation of the antisense oligonucleotides in DMEM supplemented with 10% heat-inactivated FBS in the absence (a, b) and presence (c, d) of SuperFect™.

FIGS. 10(a) and (b), which pertain to the analysis of the degradation of the oligodeoxynucleotides in the culture medium containing FBS, show that the secondary structure, of a hairpin, loop or spiral type, increases significantly the resistance to nucleases of the structured oligodeoxynucleotides. The resistance of the oligodeoxy-nucleotides with hairpin and loop to degradation depends on the type of internal duplexes and their thermal stability. For example, the half-life of the most thermostable hairpin H10 (SEQ. ID. NO. 12) is greater than that of the hairpins H6 (SEQ. ID. NO. 10) and H8 (SEQ. ID. NO. 11). At the same time, the oligodeoxynucleotide L10 (SEQ. ID. NO. 15) with a loop is as resistant to degradation as the oligodeoxynucleotide H8 (SEQ. ID. NO. 11) with a hairpin while its thermal stability is inferior (53° C. for L10 (SEQ. ID. NO. 15) and 60° C. for H8 (SEQ. ID. NO. 11)). All of the linear oligonucleotides 21L (SEQ. ID. NO. 7), 55L (SEQ. ID. NO. 8), and 21PS (SEQ. ID. NO. 9) are rapidly degraded. These results confirm the previously reported data regarding the very short half-lives of the linear phosphorothioate and phosphodiester oligonucleotides in serum [10, 11].

Various transfection reagents can be used in order to augment the penetration of the oligonucleotides into the cells [38–42]. The influence of one of these agents, a dendrimer molecule named SuperFect™, on the stability of oligodeoxynucleotides was investigated in DMEM supplemented with 10% FBS. As shown in FIGS. 10(c) and (d), the complexes formed by the oligodeoxynucleotides with SuperFect™ present greater resistance to nucleolytic degradation than the oligodeoxynucleotides alone. The augmentation of the resistance is most significant with the linear oligodeoxynucleotides 55L (SEQ. ID. NO. 8) and 21PS (SEQ. ID. NO. 9). For example, the half-life of the phosphorothioate oligodeoxy-nucleotide 21PS (SEQ. ID. NO. 9) with and without SuperFect™ is from about 12 hours to 30 minutes, respectively. The same augmentation of the stability was observed with 55L (SEQ. ID. NO. 8) as is shown in FIGS. 10(a) and (c). This is in agreement with the data known from the literature showing that the formation of complexes of polyamine compounds with oligodeoxynucleotides augments their stability in relation to nucleases [38]. Moreover, the half-life of unmodified oligodeoxynucleotide 21L (SEQ. ID. NO. 7) with and without SuperFect™ is essentially identical. It is possible that the complex formed by SuperFect™ with this short oligodeoxynucleotide does not sufficiently protect the ends of the oligodeoxynucleotide which undergo enzymatic degradations.

The stability of the oligodeoxynucleotides in the lysates of the cells HeLa and NIH 3T3 varies with the type of lysate. It should be noted that these lysates have identical concentrations of protein. Consequently, the distinctions between their nucleolytic activities depends on their quantitative or qualitative differences in terms of activity of the nucleases. FIGS. 11(a) and (b) show that the degradation is more rapid in the HeLa lysate. All of the linear oligodeoxynucleotides, 21L (SEQ. ID. NO. 7), 21PS (SEQ. ID. NO. 9) and 55L (SEQ. ID. NO. 8), are rapidly degraded, with half-lives extending about 10 minutes.

With regard to the NIH 3T3 lysate, FIGS. 11(c) and (d) show that the degradation rate of the structured oligodeoxynucleotides is lower than in the HeLa lysate. Interestingly, the structured oligodeoxynucleotides Dh6 (SEQ. ID. NO. 13), L8 (SEQ. ID. NO. 14) and L10 (SEQ. ID. NO. 15), all with 5' and 3' protection, are more stable than the structured oligodeoxynucleotides H6 (SEQ. ID. NO. 10), H8 (SEQ. ID. NO. 11) and H10 (SEQ. ID. NO. 12), which have a hairpin at the 3' end only. These results suggest that the contribution of the 5' exonucleases activity to the degradation of the oligonucleotide is very large in this lysate. Nevertheless, modification by a terminal phosphorothioate does not have a significant influence on the resistance of the oligodeoxynucleotide, compared to the oligodeoxynucleotides 21L (SEQ. ID. NO. 7) and 21PS (SEQ. ID. NO. 9).

FIG. 12 presents the performance of the oligodeoxynucleotides in the two cell lines HeLa and 3T3. In order to improve the penetration of the oligodeoxynucleotides into the cells, their complexes with the transfection agent SuperFect™ were formed and incubated with the cells. FIGS. 12(b) and (d) show that only traces of 21L (SEQ. ID. NO. 7) were found in the two cell types after 16 hours of incubation. In contrast, FIGS. 12(a) to (b) show that significant quantities (50 to 80%) of the other oligodeoxynucleotides, including the linear oligodeoxynucleotides 55L (SEQ. ID. NO. 8) and 21PS (SEQ. ID. NO. 9), were detected in the cells. After 48 hours of incubation, the quantity of intact oligodeoxynucleotides in the interior of the cells diminishes but remains at a level of 20 to 30%. FIGS. 12 (a), (b) and (c), (d) show that there is no significant difference between the two cell lines. All of the oligodeoxynucleotides with a secondary structure have the same stability which is greater than the stability of the linear oligodeoxynucleotides 55L (SEQ. ID. NO. 8) and 21PS (SEQ. ID. NO. 9).

Example 2

Inhibition of the Protein Expression of the Reporter Gene pEGFP-N1

This example presents the results of the β-gal/pEGFP-N1 test on HeLa cells.

Table 2 below shows the characteristics of the oligonucleotides used in this example, the sequences of which are presented in attached FIG. 13.

TABLE 2

| Oligonucleotide | $T_m$, ° C., 50 mM NaCl, 10 mM phosphate (pH 7.0) | $T_m$, ° C., 150 mM NaCl, 5 mM $MgCl_2$, 10 mM Tris-HCl (pH 7.0) | Possible structure at 37° C. |
| --- | --- | --- | --- |
| Dh INGFp | 60 | 71 | Hairpin |
| Sh-6 INGFp | 56 | 68 | Hairpin |
| L2 INGFp | 50 | 56 | Stem-loop |
| L2 INGFp 2S | 48 | 56 | Stem-loop |
| L4 INGFp 2S | 55 | 63 | Stem-loop |
| SDh INGFp | 32, 45 | 58 | Hairpin |
| L4 INGFp | 56 | 64 | Stem-loop |
| L7 INGFp | 52 | 60 | Stem-loop |
| C7 INGFp | 50 | 57 | Stem-loop |
| 21 PS | — | 30 | Linear |

The present example also presents the results obtained by introducing into three antisense oligonucleotides of the invention the phosphorothioate nucleotides marked by * in FIG. 13.

Table 3 below presents the inhibition of protein expression of the reporter gene pEGFP-N1 (in %) by the phosphodiester and phosphorothioate oligonucleotides.

TABLE 3

| Phosphodiester oligonucleotides | (%) | Phosphorothioate oligonucleotides | (%) |
| --- | --- | --- | --- |
| Dh INGFp | 15–25 | | |
| Sh-6 INGFp | 15–25 | | |
| L2 INGFp | 5–10 | L2 INGFp 2S | 65–80 |
| L4 INGFp | 15–25 | L4 INGFp 2S | 30–40 |
| L7 INGFp | 10–15 | | |
| C7 INGFp (negative control) | 0 | 21 PS (negative control) | 0 |
| | | SDh INGFp | 15–30 |

Example 3

Study of Antisense Oligonucleotides of the Invention Comprising a Region Complementary to the Oncogene EWS-Fli1 of Ewing's Sarcoma 1) Selection of the Antisense Oligonucleotides According to the Invention EWS-Fli1 (SEQ. ID. NO. 25) is the oncogenous gene of Ewing's sarcoma (solid and hematologic tumor of the child) and neuroectodermal primitive tumors.

In order to inhibit the EWS-Fli1 gene, RNA was selected as the target because it produces a chimeric protein EWS-Fli1. This protein, responsible for the disease, induces the development of Ewing's sarcoma (Tanaka, K., Iwakuma, T., Harimaya, K., Sato, H., Iwamoto, Y. J. Clin Invest. 1997, 239–247; Toreetsky, J. A., Connell, Y., Neckers, L., Bhat, K. J. Neuro-Oncology 1997, 31, 9–16). The RNA is constituted by half of the recombination 5' EWS (gene of chromosome 22) with half of the recombination 3' (Fli1 gene of chromosome 11). A translocation of chromosomes 22 and 11 is required in order to create a 22/11 chimera.

The protein oncogene contains 1500 bases. In order to inhibit the oncogene it is necessary to use antisense oligonucleotides centered on the "break point" of the fusion oncogene. In the articles of the prior art (Tanaka, K., Iwakuma, T., Harimaya, K., Sato, H., Iwamoto, Y. J. Clin Invest. 1997, 239–247; Toreetsky, J. A., Connell, Y., Neckers, L., Bhat, K. J. Neuro-Oncology 1997, 31, 9–16), the authors identify the phosphorothioate oligonucleotides capable of inhibiting the chimeric oncogene in vitro and in vivo: these oligonucleotides are linear.

In the context of the present invention, antisense phosphorothioate oligonucleotides structured with a secondary structure were prepared with the dual goals of protecting the antisense from degradation and facilitating its interaction with the target and its in vitro and in vivo efficacy.

Figure 14:
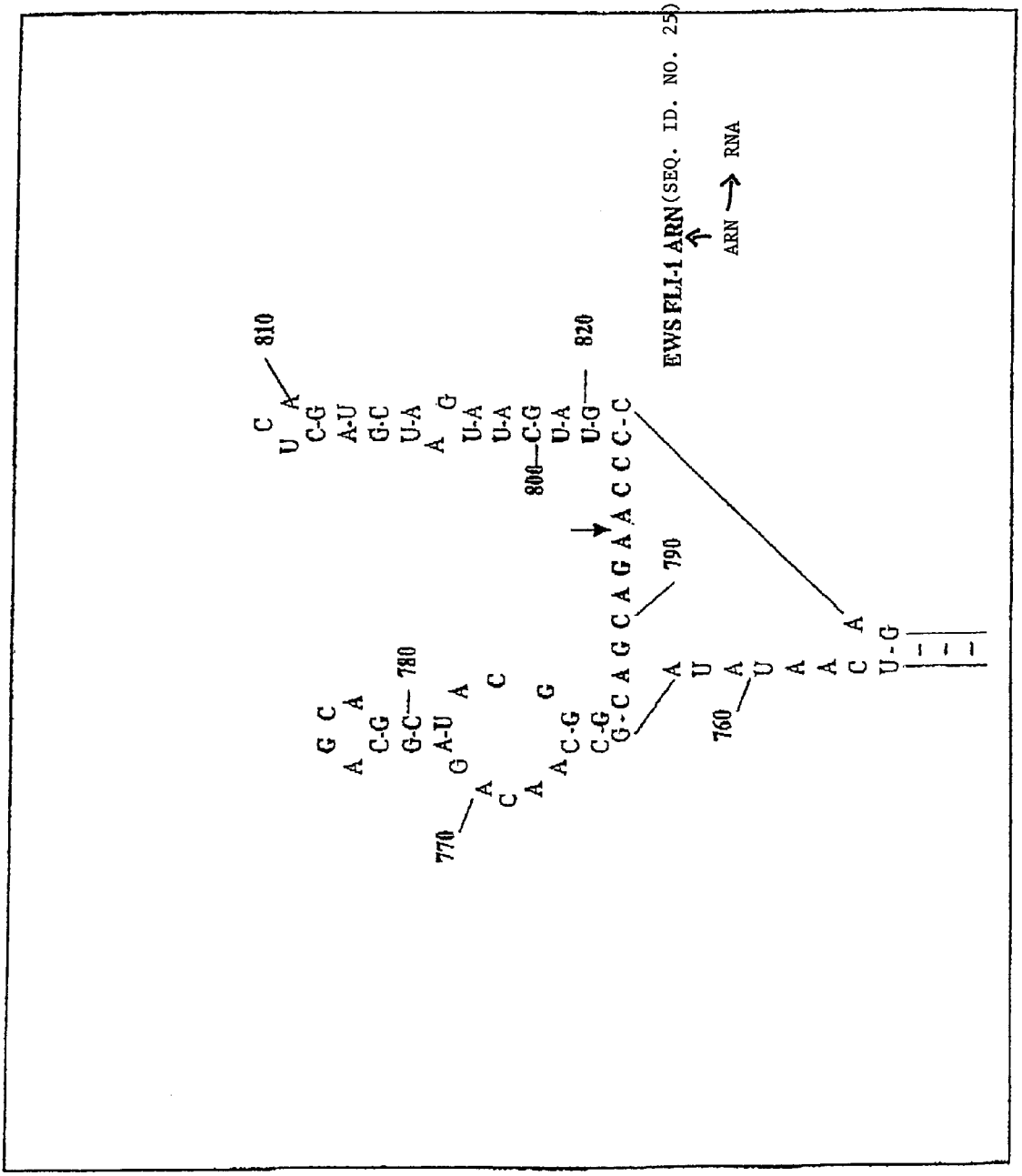
FIG. 14 shows the secondary structure of the target EWS-Fli1 RNA (SEQ. ID. NO. 25) analyzed in Example 3.

So as to select the secondary structure the most suitable for the target, the secondary structure of this target was calculated using the program "RNA Structure 3.21". Attached FIG. 14 shows the structure of this target. All of the sequences of the EWS-Fli1 RNA (SEQ. ID. NO. 25) were analyzed and six secondary structures conserved the structures of the target. The structured antisense oligonucleotides according to the invention selected against this target are of two types.

A first type designated EF 2929AS (SEQ. ID. NO. 10, whose structure is shown in attached FIG. 15A, was prepared. This type does not use any attached element in relation to the target in order to create the secondary structure. FIG. 15B shows the interactions with the target. It forms at 3' a structure with a loop that interacts with the target and also at 5' another interaction with a loop of the target. The structured oligonucleotides EF 2929AS (SEQ. ID. NO. 1) therefore presents itself as a complementary succession of the target. With this new conception, the interactions with the target are multiple, on the one hand at 3' with a loop and on the other hand at 5' "single stranded" on a loop of the target itself.

A second type of antisense oligonucleotide according to the invention, the structure of which is shown in attached FIG. 16A, was prepared by a adding a supplementary secondary structure to each 3' and 5' end. The interaction is implemented both with the secondary structure internally and the target externally at multiple levels. FIG. 16B shows the interactions with the target.

Thus, a structured antisense oligonucleotide was prepared with a single secondary structure added at 5', designated EF 3008AS (SEQ. ID. NO. 2). Like the oligonucleotide EF 2929AS (SEQ. ID. NO. 1), the oligonucleotide EF 3008AS (SEQ. ID. NO. 2) was conceived such that, due to its secondary structure, it would interact not only within the structured oligonucleotide but also so as to have multiple interactions at multiple levels within the target.

The various structured oligonucleotides that were created were tested on the level of protection of the in vitro and in vivo activity. Administration with nanoparticles (Transdrug®) or a vector called SuperFect® was also studied on the levels of protection and efficacy.

The sequences of the oligonucleotides EF 2929AS (SEQ. ID. NO. 1) and 3008AS (SEQ. ID. NO. 2) and the corresponding controls (SEQ.ID.NO.3 and 4) are shown in FIG. 17 in which * represents the phosphorothioate groups.

The sequence of the oligonucleotide EF 2929AS is shown in the attached sequence listing as SEQ. ID. NO. 1 and the sequence of the oligonucleotide 3008AS is shown in the attached sequence listing as SEQ. ID. NO. 2.

2) Results a) Resistance to Degradation

The capacity of the oligonucleotides EF 2929AS (SEQ. ID. NO. 1) and EF 3008AS (SEQ. ID. NO. 2), created with a secondary structure according to the invention so as to resist enzymatic hydrolysis, was studied in DMEM supplemented with 10% of newborn calf serum (called NCS: heat-inactivated newborn calf serum) and human serum (MH). So as to avoid cleavage of the phosphate labeled with ($^{32}$P), oligonucleotides with a phosphate protected at 5' by an ethyl residue were used in this study.

FIG. 18 (in A: 3008AS and in B: 2929AS) pertains to the analysis of the degradation of the oligonucleotides in the culture medium containing newborn calf serum (NCS) or human serum (MH). It shows that the secondary structure augments significantly the resistance of the oligonucleotides to the nucleases.

Two PIHCA (Transdrug®) nanoparticles with a size of 65 nm (CD2) and 100 nm (CD3) were prepared according to the Monza patent (BioAlliance); a preparation of oligonucleotides adsorbed on these nanoparticles was created. The influence of this preparation with the nanoparticles on the stability of the oligonucleotides in DMEM supplemented with 10% of newborn calf serum, NCS, and human serum, MH, was investigated. As can be seen in FIG. 18, the complexes formed by the oligonucleotides adsorbed with the nanoparticles exhibit a greater resistance to nucleotide degradation than the oligonucleotides alone.

b) Biological Efficacy

The following method was employed for measuring the inhibition of cellular proliferation:

Day 1: 100,000 EWS/Fli1 and 3T3 cells per well were distributed in 6-well plates (2 wells for one point).

Day 2: The cells were washed with PBS and 600 µl of a 10% solution of newborn calf serum (NCS) was added.

Oligodeoxynucleotide complexes created with SuperFect™ or Transdrug® (BioAlliance Pharma) diluted in 200 µl of medium without either NCS or antibiotics were added to the cells. Complete medium was added to each well so as to have a final volume of 800 µl.

Day 3: After incubation with the oligodeoxynucleotides (16 hours after transfection), the cells were washed with PBS and 1 ml of a 10% solution of NCS was added. In the evening, the cells were washed with PBS and 600 µl of a 10% solution of NCS was added.

The oligodeoxynucleotides with SuperFect™ diluted in 200 µl of medium without either NCS or antibiotics were added to the cells. Complete medium was added in each well so as to have a final volume of 800 µl.

Day 4: After incubation with the oligodeoxynucleotides (16 hours after transfection), the cells were washed with PBS and 400 µl of trypsin was added. The growth of the cells was then calculated.

An inhibitory effect of the oligonucleotides was calculated as:

I (AO)=[$N_1$(AO)–$N_0$(AO)]/N, in which

N —number of cells without oligonucleotides $N_0$(AO)—number of cells before transfection $N_1$(AO)—number of cells 2 days after the first transfection.

Figure 19:
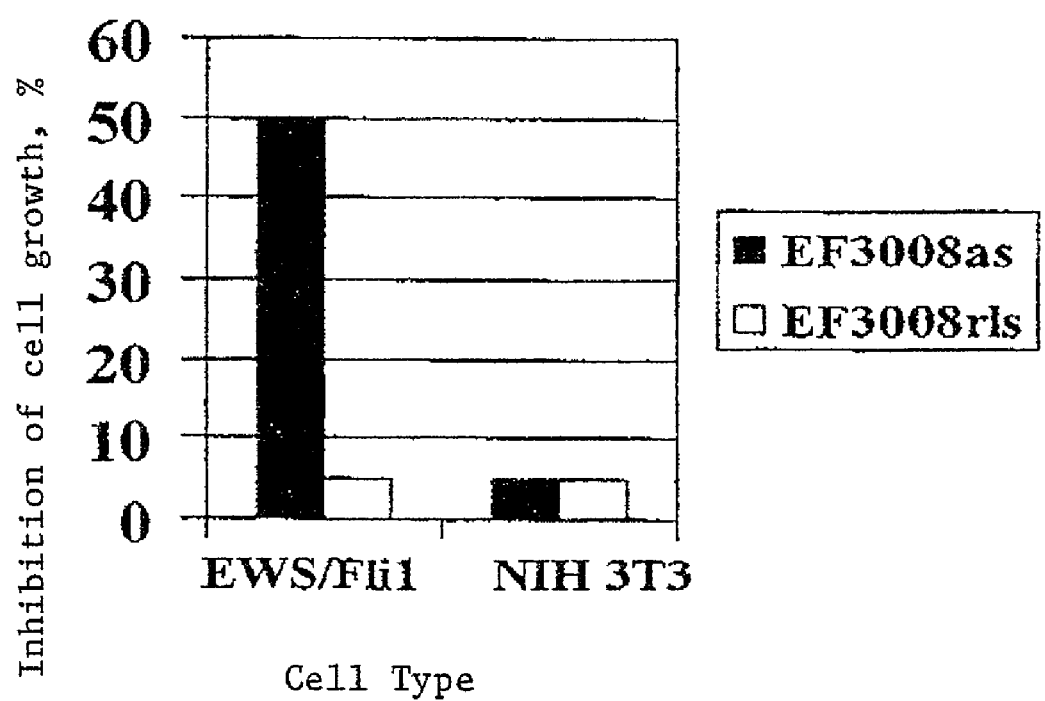
FIG. 19 illustrates inhibition of cellular proliferation on 3T3 cells expressing EWS/Fli1 by oligonucleotides EF 3008AS (SEQ. ID. NO. 2) and EF 3008RLS (SEQ. ID. NO. 3) in comparison to control 3T3 cells.

The inhibition of cellular proliferation was implemented on 3T3 cells expressing EWS/Fli1. A control with normal 3T3 cells made it possible to measure the impact of the inhibition of cell growth. These results are shown in attached FIG. 19. It can be clearly seen that the structured antisense oligonucleotide EF 3008AS (SEQ. ID. NO. 2) is active with regard to this criterion, compared to the negative control of the structured oligonucleotide which has an inverted sequence EF 3008RLS (SEQ. ID. NO. 3). It can be seen that EF 3008AS (SEQ. ID. NO. 2) induces 50% inhibition of cell growth.

c) In Vivo Model of Ewing's Sarcoma

The study was performed on transgenic mice (nude mouse, model developed by the C. Auflair F. Subra team) which expresses EWS/Fli1 (SEQ. ID. NO. 25) and which presents the disease in the tumor form (Ewing's sarcoma). This palpable tumor appears within 14 to 28 days after injection of the tumoral cells.

The protocol described below was employed.

Male nude mice aged 6 weeks were prepared. They received EWS/Fli1 cells from cell cultures which were resuspended at the rate of 5·10$^6$ cells per ml in PBS. 200 microliters of this solution were injected into each mouse (groups of 3 mice per type of treatment tested). 14 to 28 days after the inoculation, the treatments were injected via the intratumoral route into a tumor with a size of 2 to 4 mm$^3$, then 4 more injections were implemented on days 5, 8, 12 and 15 after the first injection. The animals were sacrificed 21 days after the final injection.

The tumoral volume was evaluated during the experimentation by two perpendicular measurements (length L and width W; calculation of LW2/2).

The treatment groups presented in FIG. 20 and 21 are as follows:

Group 1: control mice without injection of oligonucleotides.

Group 2: mice 1, 2, 3. Structured antisense oligonucleotides: 100 microliters of PBS containing 20 micrograms of oligonucleotides EF 3008AS (SEQ. ID. NO. 2) adsorbed on nanoparticles (50 micrograms/ml) and 50 micromoles of CTAB. Size of nanoparticles was 65 nanometers.

Group 3: mice 1c, 2c, 3c. Negative control oligonucleotides EF 3008RLS (SEQ. ID. NO. 3) under the same conditions with 65-nanometer nanoparticles.

Group 4: mice 1, 2, 3. Structured antisense oligonucleotides: 100 microliters or PBS containing 20 micrograms of oligonucleotides EF 3008AS (SEQ. ID. NO. 2) adsorbed on nanoparticles (50 micrograms/ml) and 50 micromoles of CTAB. Size of nanoparticles: 100 nanometers.

Group 5: mice 1c, 2c, 3c. Negative control oligonucleotides EF 3008RLS (SEQ. ID. NO. 3) under the same conditions with 100-nanometer nanoparticles.

Group 6: mice 1, 2, 3. Structured antisense oligonucleotides: 100 microliters of PBS containing 20 micrograms of oligonucleotides EF 3008AS (SEQ ID. NO. 2) injected with 54 micrograms.

Group 7: mice 1AS, 2AS, 3AS. Negative control oligonucleotides EF 3008RLS (SEQ. ID. NO. 3) under the same conditions without SuperFect™.

One can see in vivo efficacy with a stabilization of the tumor growth from the intratumoral injection of structured oligonucleotides according to the invention compared with the negative controls. This effect can also be seen when these structured oligonucleotides are administered with a conventionally employed vector or using nanoparticles of different size so as to facilitate intracellular entry of the oligonucleotides.

BIBLIOGRAPHIC REFERENCES

1. Curcio L. D.; Bouffard D. Y.; Scanlon K. J. Pharmacol. Ther., 1997, 74, 317–332.
2. Wyngaarden J.; Potts J.; Cotter F.; Martin R. R.; Mehta V.; Agrawal S.; Eckstein F.; Levin A.; Black L.; Cole R.; Crooke S.; Kreig A.; Diasio R.; Gait M. J.; Nature Biotech., 1997, 15, 519–524.
3. Agrawal S; Trends Biotech., 1996, 14, 376–387.
4. Agrawal S.; Prospect for Antisense Nucleic Acid Therapy of Cancer and AIDS, 1991, 143–158
5. Leiter J. M. E.; Agrawal S.; Palese P.; Zamecnik P. C.; Proc. Natl. Acad. Sci. U.S.A., 1990, 87, 3430–3434
6. Pagano J. S.; Jimenez G.; Sung N. S.; Raab-Traub N.; Lin J. -C.; Antisense Strategies. R., 1992, 107–116
7. Steele C.; Cowsert L. M.; Shillitoe E. J.; Cancer Res., 1993, 53, 2330–2337
8. Storey A.; Oates D.; Banks L.; Crawford L.; Crook T.; Nucl. Acids. Res., 1991, 19(15), 4109–4114
9. Kulka M.; Smith C. C.; Aurelian L., Fishelevich R.; Meade K.; Miller P.; TS'O P. O. P.; Proc. Natl. Acad. Sci. U.S.A, 1989, 86, 6868–6872
10. Hoke, G. D.; Draper, K.; Freier, S. M.; Gonzalez. C.; Driver, V. B.; Zounes, M. C.; Ecker, D. J. Nucleic Acids Res., 1991, 19, 5743–5748.
11. Wickstrom E.; J. Biochem. Biophys. Methods, 1986, 13, 97–102.
12. Eder P. S.; Devine R. J.; Dagle J. M.; Walder J. A.; Antisense Res. Dev., 1991, 1, 141–151.
13. Stephenson M. L.; Zamecnik P. C.; ; Proc. Natl. Acad. Sci. U.S.A., 1978, 75, 285–288
14. Bonfils E.; Depierreux C.; Midoux P.; Thoung N. T.; Monsigny M.; Roche A. C.; Nucl. Acids. Res., 1992, 20(17), 4621–4629
15. Wagner E.; Cotten M.; Mechtler K.; Kirlappos H.; Birnstiel M. L.; Bioconjugate Chem., 1991, 2, 226–231
16. Leonetti J. P.; Degols G.; Lebleu B.; Bioconjugate Chem., 1993, 1, 149–153
17. Perrouault L.; Asseline U.; Rivalle C.; Thoung N. T.; Bisagni E.; Giovannangeli C.; Le Doan T.; Héline C.; Nature, 1990, 344, 358–360
18. Camper H. B.; Reed M. W.; Cox T.; Virosco J. S.; Adams A. D.; Gall A. A.; Scholer J. K.; Meyer R. B. J.; Nucl. Acids. Res., 1993, 21(1), 145–150
19. Ortigao J. F. R.; Rösch H.; Selter H.; Fröhlich A.; Lorenz A.; Montenarh M.; Seliger H.; Antisense Res. Dev., 1992, 2, 129–146
20. Schaw, J. -P.; Kent K.; Bird J.; Pishback J.; Froechler B.; Nucleic Acids Res., 1991, 19, 747–750.
21. Uhmaln E.; Peyman A.; Chem. Reviews, 1990, 90, 544–584.
22. Stein C. A.; Cohen J. S.; Cancer Res., 1998, 48, 2659–2668.
23. Nielsen P. E.; Ann. Rev. Biophys. Biomol. Struct., 1995, 24, 167–183.
24. Morvan F.; Porumb M.; Degols G.; Lefebvre I.; Pompon A.; Sproat B. S.; Rayner B.; Malvy C.; Lebleu B.; Imbach J. -L.; J. Med. Chem., 1993, 36,.280–283.
25. Stein C. A.; Chemistry & Biology, 1996, 3, 319–323.
26. Agrawal S.; Zhao Q.; Jiang Z.; Oliver C.; Giles H.; Heath J.; Serota D.; Antisense & Nucl. Acid Drug Dev., 1997, 7, 575–584.
27. Branch A. D. TiBS, 1998, 23, 45–50.
28. Jansen B.; Wadl H.; Inoue S. A.; Trulzsch B.; Selzer E.; Duchene M.; Fichler H.; Wolf K.; Pehamberger H.; Antisense Res. Dev., 1995, 5, 271–277.
29. Henry S. P.; Zuckerman J. E.; Rojko J.; Hall W. S.; Harman R. J.; Kitchen D.; Crooke S. T. Anti-Cancer Drug Design, 1997, 12, 1–4.
30. Khan I. M.; Coulson M.; Nucl. Acids Res., 1993, 21, 2957–2958.
31. Poddevin B.; Meguenni S.; Elias I.; Vasseur M.; Blumenfeld M., Antisense Res. Dev., 1994, 4, 147–154.
32. Yoshizawa S.; Ueda T.; Ishido Y.; Miura K-i.; Watanabe F.; Hirao I.; Nucl. Acids Res., 1994, 22, 2217–2221.
33. Tang J. Y.; Teinsamani J.; Agrawal S.; Nucl. Acids Res., 1993, 21, 2739–3735.
34. Kuwasaki T.; Hosono K.; Takai K.; Ushijima K.; Nakashima H.; Saito T.; Yamamoto N.; Takaku H.; Biochem. Biophys. Res. Com., 1996, 228, 623–631.
35. Barker R. H.; Metelev V.; Coakley A.; Zanecnik P.; Exp. Parasitology, 1998, 88, 51–59.
36. Xodo L. E.; Manzini G.; Quadrifoglio P.; van der Marel G. A.; van Boom J. H.; Biochimie, 1989, 71, 793–803.
37. Petersheim M.; Turner D. H.; Biochem., 1982, 22, 256–263.
38. Capaccioli S.; Di Pasquale G.; Mini E.; Mazzei T.; Quattrone A.; Biolochem. and Biophys. Res. Com, 1993, 197, 818–825.
39. Chavany C.; Saison-Behmoaras T.; Le Doan T.; Puiseux F.; Couvareur P.; Helene C.; Pharm. Res., 1994, 11, 1370–1378.
40. Delong R.; Stephenson K.; Loftus T.; Fisher M.; Alahari S.; Nolting A.; Juliano R. L.; .J. Pharm. Sci., 1997, 86, 762–764.
41. Morris M. C.; Vidal P.; Chaloin L.; Heitz F.; Divita G.; Nucleic Acids Res., 1997, 25, 2730–2736.
42. Poxon S. W.; Mitchell P. M.; Liang E.; Hughes J. A.; Drug Delivery, 1996, 3, 255–261.
43. Couch R. J.; New Biologist, 1990, 2, 771–777.
44. Kukowska-Latallo J. F.; Bielinska A. U.; Jonson J.; Spindler R.; Tomalia D. A.; Baker J. R.; Proc. Natl. Acad. Sci. USA, 1996, 93, 4897–4902.
45. Bielinska A.; Kukowska-Latallo J. F.; Jonson J.; Tomalia D. A.; Baker J. R.; Nucleic Acids Res., 1996, 24, 2176–2182.
46. Tang M. X.; Redemann C. T.; Szoka F. C.; Bioconjugate Chem., 1996, 7, 703–714.

We claim:

1. An oligonucleotide comprising an antisense sequence and at least one secondary structure, wherein said secondary structure disintegrates upon attachment of the oligonucleotide to a target nucleic acid, wherein said oligonucleotide is SEQ ID NO: 2.

2. The oligonucleotide according to claim 1, wherein said secondary structure is one selected from the group consisting of a hairpin, a loop and a spiral.

3. The oligonucleotide according to claim 1, wherein said oligonucleotide further comprises at the 3' and 5' ends one or more modified nucleotides selected from the group consisting of phosphonate, phosphoramidate and phosphorothioate modified nucleotides.

4. A composition comprising one or more oligonucleotides according to claim 1 and a pharmaceutically acceptable vehicle.

5. The composition according to claim 4, wherein the form of said oligonucleotide is one selected from the group consisting of free, encapsulated, bound, and conjugated to one or more substances.

6. The composition according to claim 5, wherein said substance to which said oligonucleotide is conjugated is one or more selected from the group consisting of an antibody, a liposome, a microsphere, a microorganism, a cell, a nanoparticle, a dendrimer, a cationic lipid and a peptide.

* * * * *